US009943654B2

(12) United States Patent
Herrmann et al.

(10) Patent No.: US 9,943,654 B2

(45) Date of Patent: Apr. 17, 2018

(54) NEBULIZER

(75) Inventors: Frank Herrmann, Duisburg (DE); Holger Krenz, Dortmund (DE); Guido Endert, Leichlingen (DE); Horst Wergen, Wuppertal (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 575 days.

(21) Appl. No.: 13/702,362

(22) PCT Filed: Jun. 1, 2011

(86) PCT No.: PCT/EP2011/059088

§ 371 (c)(1),
(2), (4) Date: Mar. 20, 2013

(87) PCT Pub. No.: WO2011/160932

PCT Pub. Date: Dec. 29, 2011

(65) Prior Publication Data

US 2013/0206136 A1 Aug. 15, 2013

(30) Foreign Application Priority Data

Jun. 24, 2010 (EP) .................................... 10006584

(51) Int. Cl.

*A61M 11/02* (2006.01)
*A61M 15/00* (2006.01)
*B05B 11/00* (2006.01)

(52) U.S. Cl.

CPC ........ *A61M 11/02* (2013.01); *A61M 15/0028* (2013.01); *A61M 15/0065* (2013.01);

(Continued)

(58) Field of Classification Search

CPC .. A61M 11/00; A61M 11/006; A61M 11/007; A61M 11/06; A61M 11/08;

(Continued)

(56) References Cited

U.S. PATENT DOCUMENTS 1,828,864 A 10/1931 Hopkins
2,015,970 A 10/1935 Schoene (Continued)

FOREIGN PATENT DOCUMENTS

AU 2005201364 A1 7/2006
CA 1094549 A 1/1981

(Continued)

OTHER PUBLICATIONS

International Search Report, Form PCT/ISA/210, for corresponding PCT/EP2011/059088; dated Sep. 26, 2011.

(Continued)

*Primary Examiner* — (Jackie) Tan-Uyen T Ho
*Assistant Examiner* — Joseph D Boecker
(74) *Attorney, Agent, or Firm* — Marc Began; Philip I. Datlow

(57) ABSTRACT

A nebulizer (1), in particular inhaler, having a pre-installed container (3) is proposed. The nebulizer comprises a securing member (30) preventing fluidic connection or opening of the container in a delivery state. The securing member can be manually opened, removed, released or destroyed by torsioning, by opening along a pre-determined breaking line and/or by means of an actuator (50). This facilitates handling.

32 Claims, 17 Drawing Sheets

(52) U.S. Cl.
CPC ...... *B05B 11/0054* (2013.01); *B05B 11/3001* (2013.01); *B05B 11/308* (2013.01); *B05B 11/3059* (2013.01); *A61M 2202/0468* (2013.01); *A61M 2205/276* (2013.01)

(58) Field of Classification Search
CPC .............. A61M 15/00; A61M 15/0001; A61M 15/0086; A61M 15/009; A61M 15/06; A61M 2202/0468; A61M 2205/276; A61M 5/31571; A61M 5/50; A61M 15/0095; B05B 11/00; B05B 11/0005; B05B 11/0035; B05B 11/0054; B05B 11/06; B05B 11/3001; B05B 11/3052; B05B 11/3056; B05B 11/3057; B05B 11/3059; B05B 11/0027; B05B 11/3049
USPC ..... 128/200.14, 200.21, 203.23; 222/153.02, 222/153.04, 153.06, 153.07, 153.14
See application file for complete search history.

(56) References Cited

U.S. PATENT DOCUMENTS 2,127,401 A 8/1938 Gillican
2,161,071 A 6/1939 McGrath et al.
2,321,428 A 6/1943 Schloz
2,329,311 A 9/1943 Waters
2,362,103 A 11/1944 Smith
2,651,303 A 9/1953 Johnson et al.
2,720,969 A 10/1955 Kendall
2,793,776 A 5/1957 Lipari
2,974,880 A 3/1961 Stewart et al.
3,032,823 A 5/1962 Sherman et al.
3,157,179 A 11/1964 Allen et al.
3,172,568 A 3/1965 Modderno
3,196,587 A 7/1965 Hayward et al.
3,223,289 A 12/1965 Bouet
3,299,603 A 1/1967 Shaw
3,348,726 A * 10/1967 La Cross ............... B65D 17/16 220/270
3,354,883 A 11/1967 Southerland
3,425,591 A * 2/1969 Pugh, Sr. ............. B65D 17/163 220/270
3,440,144 A 4/1969 Anderson et al.
3,457,694 A 7/1969 Tatibana
3,491,803 A 1/1970 Galik
3,502,035 A 3/1970 Fedit
3,580,249 A 5/1971 Takaoka
3,590,557 A 7/1971 Vogel
3,606,106 A * 9/1971 Yuhas .................. B65D 83/226 222/153.07
3,632,743 A 1/1972 Geller et al.
3,655,096 A 4/1972 Easter
3,674,060 A 7/1972 Ruekberg
3,675,825 A 7/1972 Morane
3,684,124 A * 8/1972 Song ...................... B65D 83/40 220/270
3,802,604 A 4/1974 Morane et al.
3,817,416 A * 6/1974 Costa ................... B65D 47/122 215/213
3,820,698 A 6/1974 Franz
3,842,836 A 10/1974 Ogle
3,858,580 A 1/1975 Ogle
3,861,851 A 1/1975 Schiemann
3,870,147 A 3/1975 Orth
3,924,741 A 12/1975 Kachur et al.
3,933,279 A 1/1976 Maier
3,946,732 A 3/1976 Hurscham
3,949,751 A 4/1976 Birch et al.
3,951,310 A 4/1976 Steiman
3,953,995 A 5/1976 Haswell et al.
3,973,603 A 8/1976 Franz
4,012,472 A 3/1977 Lindsey
4,031,892 A 6/1977 Hurschman
4,036,439 A 7/1977 Green
4,048,997 A 9/1977 Raghavachari et al.
4,067,499 A 1/1978 Cohen
4,094,317 A 6/1978 Wasnich
4,120,995 A 10/1978 Phipps et al.
4,126,559 A 11/1978 Cooper
4,153,689 A 5/1979 Hirai et al.
4,174,035 A 11/1979 Wiegner
4,177,938 A 12/1979 Brina
4,178,928 A 12/1979 Tischlinger
4,195,730 A 4/1980 Hunt
4,245,788 A 1/1981 Wright
4,275,840 A 6/1981 Staar
4,315,570 A 2/1982 Silver et al.
4,338,765 A 7/1982 Ohmori et al.
4,377,106 A * 3/1983 Workman et al. ................ 92/23
4,434,908 A * 3/1984 French ................. B65D 17/163 220/270
4,456,016 A 6/1984 Nowacki et al.
4,458,821 A * 7/1984 Ostrowsky ............. B29C 57/00 215/252
4,463,867 A * 8/1984 Nagel ................. B65D 1/0238 215/46
4,467,965 A 8/1984 Skinner
4,474,302 A * 10/1984 Goldberg ........... B65D 39/0017 215/256
4,476,116 A 10/1984 Anik
4,515,586 A 5/1985 Mendenhall et al.
4,516,967 A 5/1985 Kopfer
4,524,888 A * 6/1985 Tada ................... B05B 11/0064 222/153.02
4,603,794 A 8/1986 DeFord et al.
4,677,975 A 7/1987 Edgar et al.
4,727,985 A 3/1988 McNeirney et al.
4,749,082 A 6/1988 Gardiner et al.
4,796,614 A 1/1989 Nowacki et al.
4,805,377 A 2/1989 Carter
4,813,210 A 3/1989 Masuda et al.
4,821,923 A 4/1989 Skorka
4,840,017 A 6/1989 Miller et al.
4,863,720 A 9/1989 Burghart et al.
4,868,582 A 9/1989 Dreinhoff
4,885,164 A 12/1989 Thurow
4,905,450 A 3/1990 Hansen et al.
4,926,613 A 5/1990 Hansen
4,951,661 A 8/1990 Sladek
4,952,310 A 8/1990 McMahan et al.
4,964,540 A 10/1990 Katz
RE33,444 E 11/1990 Lerner
4,973,318 A 11/1990 Holm et al.
4,979,941 A 12/1990 Ogle, II
4,982,875 A 1/1991 Pozzi et al.
5,014,492 A 5/1991 Fiorini et al.
5,025,957 A 6/1991 Ranalletta et al.
5,059,187 A 10/1991 Sperry et al.
5,060,791 A 10/1991 Zulauf
5,067,655 A 11/1991 Farago et al.
5,156,918 A 10/1992 Marks et al.
5,174,366 A * 12/1992 Nagakura ............... F28F 1/325 165/151
5,207,217 A 5/1993 Cocozza et al.
5,230,884 A 7/1993 Evans et al.
5,237,797 A 8/1993 Varlet
5,246,142 A 9/1993 DiPalma et al.
5,261,565 A 11/1993 Drobish et al.
5,263,842 A 11/1993 Fealey
5,271,153 A 12/1993 Reiboldt et al.
5,282,304 A 2/1994 Reiboldt et al.
5,282,549 A 2/1994 Scholz et al.
5,284,133 A 2/1994 Burns et al.
5,289,948 A 3/1994 Moss et al.
5,339,990 A 8/1994 Wilder
5,352,196 A 10/1994 Haber et al.
5,380,281 A 1/1995 Tomellini et al.
5,385,140 A 1/1995 Smith
5,394,866 A 3/1995 Ritson et al.
5,408,994 A 4/1995 Wass et al.
5,433,343 A 7/1995 Meshberg
5,435,282 A 7/1995 Haber et al.

(56) References Cited

U.S. PATENT DOCUMENTS 5,435,884 A 7/1995 Simmons et al.
5,451,569 A 9/1995 Wong et al.
5,456,522 A 10/1995 Beach
5,456,533 A 10/1995 Streiff et al.
5,472,143 A 12/1995 Bartels et al.
5,482,030 A 1/1996 Klein
5,487,378 A 1/1996 Robertson et al.
5,497,944 A 3/1996 Weston et al.
5,499,750 A 3/1996 Manifold
5,499,751 A 3/1996 Meyer
5,503,869 A 4/1996 Van Oort
5,509,404 A 4/1996 Lloyd et al.
5,518,147 A * 5/1996 Peterson et al. ......... 222/153.07
5,533,994 A 7/1996 Meyer
5,541,569 A 7/1996 Jang
5,544,646 A 8/1996 Lloyd et al.
5,547,094 A 8/1996 Bartels et al.
5,569,191 A 10/1996 Meyer
5,574,006 A 11/1996 Yanagawa
5,579,760 A 12/1996 Kohler
5,584,285 A 12/1996 Salter et al.
5,593,069 A 1/1997 Jinks
5,599,297 A 2/1997 Chin et al.
5,603,943 A 2/1997 Yanagawa
5,614,172 A 3/1997 Geimer
5,622,162 A 4/1997 Johansson et al.
5,622,163 A 4/1997 Jewett et al.
5,643,868 A 7/1997 Weiner et al.
5,662,098 A 9/1997 Yoshida
5,662,271 A 9/1997 Weston et al.
5,676,930 A 10/1997 Jager et al.
5,685,846 A 11/1997 Michaels, Jr.
5,697,242 A 12/1997 Halasz et al.
5,709,202 A 1/1998 Lloyd et al.
5,722,598 A 3/1998 Werding
5,738,087 A 4/1998 King
5,740,967 A 4/1998 Simmons et al.
5,763,396 A 6/1998 Weiner et al.
5,775,321 A 7/1998 Alband
5,782,345 A 7/1998 Guasch et al.
5,827,262 A 10/1998 Neftel et al.
5,829,435 A 11/1998 Rubsamen et al.
5,833,088 A 11/1998 Kladders et al.
5,848,588 A 12/1998 Foley et al.
5,868,287 A 2/1999 Kurokawa et al.
5,881,718 A 3/1999 Mortensen et al.
5,884,620 A 3/1999 Gonda et al.
5,902,298 A 5/1999 Niedospial, Jr. et al.
5,934,272 A 8/1999 Lloyd et al.
5,935,101 A 8/1999 Kato et al.
5,941,244 A 8/1999 Yamazaki et al.
5,950,016 A 9/1999 Tanaka
5,950,403 A 9/1999 Yamaguchi et al.
5,951,882 A 9/1999 Simmons et al.
5,964,416 A 10/1999 Jaeger et al.
5,975,370 A * 11/1999 Durliat ..................... 222/153.06
5,997,263 A 12/1999 Van Lintel et al.
6,041,777 A 3/2000 Faithfull et al.
6,041,969 A 3/2000 Parise
6,053,368 A 4/2000 Geimer
6,062,430 A 5/2000 Fuchs
6,098,618 A 8/2000 Jennings et al.
6,109,479 A 8/2000 Ruckdeschel
6,110,247 A 8/2000 Birmingham et al.
6,116,233 A 9/2000 Denyer et al.
6,119,853 A 9/2000 Garrill et al.
6,120,492 A 9/2000 Finch et al.
6,123,068 A 9/2000 Lloyd et al.
6,131,566 A 10/2000 Ashurst et al.
6,145,703 A * 11/2000 Opperman ...................... 222/82
6,149,054 A 11/2000 Cirrillo et al.
6,152,296 A 11/2000 Shih
6,171,972 B1 1/2001 Mehregany et al.
6,176,442 B1 1/2001 Eicher et al.
6,179,118 B1 1/2001 Garrill et al.
6,186,409 B1 2/2001 Srinath et al.
6,199,766 B1 3/2001 Fox et al.
6,223,933 B1 5/2001 Hochrainer et al.
6,224,568 B1 5/2001 Morimoto et al.
6,237,589 B1 5/2001 Denyer et al.
6,259,654 B1 7/2001 de la Huerga
6,267,154 B1 7/2001 Felicelli et al.
6,279,786 B1 8/2001 de Pous et al.
6,302,101 B1 10/2001 Py
6,315,173 B1 11/2001 Di Giovanni et al.
6,319,943 B1 11/2001 Joshi et al.
6,336,453 B1 1/2002 Scarrott et al.
6,341,718 B1 1/2002 Schilthuizen et al.
6,349,856 B1 2/2002 Chastel
6,352,152 B1 3/2002 Anderson et al.
6,352,181 B1 * 3/2002 Eberhard ............ B05B 11/3059
222/153.13
6,363,932 B1 4/2002 Forchione et al.
6,375,048 B1 4/2002 van der Meer et al.
6,392,962 B1 5/2002 Wyatt
6,395,331 B1 5/2002 Yan et al.
6,401,710 B1 6/2002 Scheuch et al.
6,401,987 B1 6/2002 Oechsel et al.
6,402,055 B1 6/2002 Jaeger et al.
6,405,872 B1 6/2002 Ruther et al.
6,412,659 B1 7/2002 Kneer
6,419,167 B1 7/2002 Fuchs
6,423,298 B2 7/2002 McNamara et al.
6,427,682 B1 8/2002 Klimowicz et al.
6,446,054 B1 9/2002 Mayorga Lopez
6,457,658 B2 10/2002 Srinath et al.
6,464,108 B2 10/2002 Corba
6,481,435 B2 11/2002 Hochrainer et al.
6,491,897 B1 12/2002 Freund et al.
6,503,362 B1 1/2003 Bartels et al.
6,513,519 B2 2/2003 Gallem
6,543,448 B1 4/2003 Smith et al.
6,548,647 B2 4/2003 Dietz et al.
6,550,477 B1 4/2003 Casper et al.
6,565,743 B1 5/2003 Poirier et al.
6,578,741 B2 6/2003 Ritsche et al.
6,581,596 B1 6/2003 Truitt et al.
6,584,976 B2 7/2003 Japuntich et al.
6,606,990 B2 8/2003 Stapleton et al.
6,620,438 B2 9/2003 Pairet et al.
6,626,309 B1 9/2003 Jansen et al.
6,640,805 B2 11/2003 Castro et al.
6,641,782 B1 11/2003 Mauchan et al.
6,669,176 B2 12/2003 Rock
6,679,254 B1 1/2004 Rand et al.
6,685,691 B1 2/2004 Freund et al.
6,698,421 B2 3/2004 Attolini
6,706,726 B2 3/2004 Meissner et al.
6,708,846 B1 * 3/2004 Fuchs et al. .................... 222/82
6,725,858 B2 4/2004 Loescher
6,729,328 B2 5/2004 Goldemann
6,732,731 B1 5/2004 Tseng
6,745,763 B2 6/2004 Webb
6,779,520 B2 8/2004 Genova et al.
6,789,702 B2 9/2004 O'Connor et al.
6,792,945 B2 9/2004 Davies et al.
6,823,862 B2 11/2004 McNaughton
6,825,441 B2 11/2004 Katooka et al.
6,846,413 B1 1/2005 Kadel et al.
6,866,039 B1 3/2005 Wright et al.
6,889,690 B2 5/2005 Crowder et al.
6,890,517 B2 5/2005 Drechsel et al.
6,915,901 B2 7/2005 Feinberg et al.
6,929,004 B1 8/2005 Bonney et al.
6,932,962 B1 8/2005 Backstrom et al.
6,942,127 B2 9/2005 Raats
6,964,759 B2 11/2005 Lewis et al.
6,977,042 B2 12/2005 Kadel et al.
6,978,916 B2 12/2005 Smith
6,986,346 B2 1/2006 Hochrainer et al.
6,988,496 B1 1/2006 Eicher et al.
6,994,083 B2 2/2006 Foley et al.
7,040,311 B2 5/2006 Hochrainer et al.
7,066,408 B2 6/2006 Sugimoto et al.

(56) References Cited

U.S. PATENT DOCUMENTS

| | | | |
|---|---|---|---|
| 7,090,093 B2 | 8/2006 | Hochrainer et al. | |
| 7,131,441 B1 | 11/2006 | Keller et al. | |
| 7,152,760 B1 * | 12/2006 | Peabody | B65D 41/48 222/153.07 |
| 7,258,716 B2 | 8/2007 | Shekarriz et al. | |
| 7,314,187 B2 | 1/2008 | Hochrainer et al. | |
| 7,331,340 B2 | 2/2008 | Barney | |
| 7,341,208 B2 | 3/2008 | Peters et al. | |
| 7,380,575 B2 | 6/2008 | Stricklin | |
| 7,417,051 B2 | 8/2008 | Banholzer et al. | |
| 7,451,876 B2 | 11/2008 | Bossi et al. | |
| 7,451,885 B2 * | 11/2008 | Nyman | B65D 1/0246 215/252 |
| 7,470,422 B2 | 12/2008 | Freund et al. | |
| 7,556,037 B2 | 7/2009 | Klein | |
| 7,559,597 B2 | 7/2009 | Mori | |
| 7,571,722 B2 | 8/2009 | Wuttke et al. | |
| 7,579,358 B2 | 8/2009 | Boeck et al. | |
| 7,611,694 B2 | 11/2009 | Schmidt | |
| 7,611,709 B2 | 11/2009 | Bassarab et al. | |
| 7,621,266 B2 | 11/2009 | Kladders et al. | |
| 7,645,383 B2 | 1/2010 | Kadel et al. | |
| 7,652,030 B2 | 1/2010 | Moesgaard et al. | |
| 7,665,461 B2 | 2/2010 | Zierenberg et al. | |
| 7,681,811 B2 | 3/2010 | Geser et al. | |
| 7,686,014 B2 | 3/2010 | Boehm et al. | |
| 7,717,299 B2 * | 5/2010 | Greiner-Perth | 222/162 |
| 7,723,306 B2 | 5/2010 | Bassarab et al. | |
| 7,743,945 B2 | 6/2010 | Lu et al. | |
| 7,779,838 B2 | 8/2010 | Hetzer et al. | |
| 7,802,568 B2 | 9/2010 | Eicher et al. | |
| 7,819,342 B2 | 10/2010 | Spallek et al. | |
| 7,823,584 B2 | 11/2010 | Geser et al. | |
| 7,837,235 B2 | 11/2010 | Geser et al. | |
| 7,849,851 B2 | 12/2010 | Zierenberg et al. | |
| 7,896,264 B2 | 3/2011 | Eicher et al. | |
| 7,980,243 B2 | 7/2011 | Hochrainer | |
| 7,994,188 B2 | 8/2011 | Disse | |
| 8,062,626 B2 | 11/2011 | Freund et al. | |
| 8,104,643 B2 * | 1/2012 | Pruvot | B05B 11/3059 222/153.06 |
| 8,167,171 B2 | 5/2012 | Moretti | |
| 8,298,622 B2 | 10/2012 | Nakayama et al. | |
| 8,479,725 B2 | 7/2013 | Hausmann et al. | |
| 8,495,901 B2 | 7/2013 | Hahn et al. | |
| 8,650,840 B2 | 2/2014 | Holakovsky et al. | |
| 8,651,338 B2 | 2/2014 | Leak et al. | |
| 8,656,910 B2 | 2/2014 | Boeck et al. | |
| 8,733,341 B2 | 5/2014 | Boeck et al. | |
| 8,734,392 B2 | 5/2014 | Stadelhofer | |
| 8,944,292 B2 * | 2/2015 | Moreau | B05B 11/3049 215/252 |
| 8,950,393 B2 | 2/2015 | Holakovsky et al. | |
| 8,960,188 B2 | 2/2015 | Bach et al. | |
| 8,997,735 B2 | 4/2015 | Zierenberg et al. | |
| 9,027,854 B2 | 5/2015 | Moser et al. | |
| 9,192,734 B2 | 11/2015 | Hausmann et al. | |
| 9,238,031 B2 | 1/2016 | Schmelzer et al. | |
| 9,744,313 B2 | 8/2017 | Besseler et al. | |
| 2001/0008632 A1 | 7/2001 | Freund et al. | |
| 2001/0028308 A1 | 10/2001 | De La Huerga | |
| 2001/0032643 A1 | 10/2001 | Hochrainer et al. | |
| 2001/0035182 A1 | 11/2001 | Rubin et al. | |
| 2002/0000225 A1 | 1/2002 | Schuler et al. | |
| 2002/0005195 A1 | 1/2002 | Shick et al. | |
| 2002/0007155 A1 | 1/2002 | Freund et al. | |
| 2002/0046751 A1 | 4/2002 | MacRae et al. | |
| 2002/0060255 A1 | 5/2002 | Benoist | |
| 2002/0074429 A1 | 6/2002 | Hettrich et al. | |
| 2002/0079285 A1 | 6/2002 | Jansen et al. | |
| 2002/0092523 A1 | 7/2002 | Connelly et al. | |
| 2002/0111363 A1 | 8/2002 | Drechsel et al. | |
| 2002/0129812 A1 | 9/2002 | Litherland et al. | |
| 2002/0130195 A1 | 9/2002 | Jaeger et al. | |
| 2002/0137764 A1 | 9/2002 | Drechsel et al. | |
| 2002/0176788 A1 | 11/2002 | Moutafis et al. | |
| 2003/0039915 A1 | 2/2003 | Holt et al. | |
| 2003/0064032 A1 | 4/2003 | Lamche et al. | |
| 2003/0066524 A1 | 4/2003 | Hochrainer et al. | |
| 2003/0066815 A1 * | 4/2003 | Lucas | B65D 41/48 215/253 |
| 2003/0080210 A1 | 5/2003 | Jaeger et al. | |
| 2003/0085254 A1 | 5/2003 | Katooka et al. | |
| 2003/0098023 A1 | 5/2003 | Drachmann et al. | |
| 2003/0106827 A1 | 6/2003 | Cheu et al. | |
| 2003/0145849 A1 | 8/2003 | Drinan et al. | |
| 2003/0178020 A1 | 9/2003 | Scarrott | |
| 2003/0181478 A1 | 9/2003 | Drechsel et al. | |
| 2003/0183225 A1 | 10/2003 | Knudsen | |
| 2003/0187387 A1 | 10/2003 | Wirt et al. | |
| 2003/0191151 A1 | 10/2003 | Chaudry et al. | |
| 2003/0194379 A1 | 10/2003 | Brugger et al. | |
| 2003/0196660 A1 | 10/2003 | Haveri | |
| 2003/0209238 A1 | 11/2003 | Peters et al. | |
| 2003/0226907 A1 | 12/2003 | Geser et al. | |
| 2004/0004138 A1 | 1/2004 | Hettrich et al. | |
| 2004/0010239 A1 | 1/2004 | Hochrainer et al. | |
| 2004/0015126 A1 | 1/2004 | Zierenberg et al. | |
| 2004/0019073 A1 | 1/2004 | Drechsel et al. | |
| 2004/0055907 A1 * | 3/2004 | Marco | B65D 71/504 206/150 |
| 2004/0060476 A1 | 4/2004 | Sirejacob | |
| 2004/0069799 A1 | 4/2004 | Gee et al. | |
| 2004/0092428 A1 | 5/2004 | Chen et al. | |
| 2004/0094147 A1 | 5/2004 | Schyra et al. | |
| 2004/0134494 A1 | 7/2004 | Papania et al. | |
| 2004/0134824 A1 | 7/2004 | Chan et al. | |
| 2004/0139700 A1 | 7/2004 | Powell et al. | |
| 2004/0143235 A1 | 7/2004 | Freund et al. | |
| 2004/0164186 A1 | 8/2004 | Kladders et al. | |
| 2004/0166065 A1 | 8/2004 | Schmidt | |
| 2004/0182867 A1 | 9/2004 | Hochrainer et al. | |
| 2004/0184994 A1 | 9/2004 | DeStefano et al. | |
| 2004/0194524 A1 | 10/2004 | Jentzsch | |
| 2004/0210199 A1 | 10/2004 | Atterbury et al. | |
| 2004/0231667 A1 | 11/2004 | Horton et al. | |
| 2005/0028812 A1 | 2/2005 | Djupesland | |
| 2005/0028815 A1 | 2/2005 | Deaton et al. | |
| 2005/0028816 A1 | 2/2005 | Fishman et al. | |
| 2005/0061314 A1 | 3/2005 | Davies et al. | |
| 2005/0089478 A1 | 4/2005 | Govind et al. | |
| 2005/0098172 A1 | 5/2005 | Anderson | |
| 2005/0126469 A1 | 6/2005 | Lu | |
| 2005/0131357 A1 | 6/2005 | Denton et al. | |
| 2005/0158394 A1 | 7/2005 | Staniforth et al. | |
| 2005/0159441 A1 | 7/2005 | Hochrainer et al. | |
| 2005/0183718 A1 | 8/2005 | Wuttke et al. | |
| 2005/0191246 A1 | 9/2005 | Bechtold-Peters et al. | |
| 2005/0194472 A1 | 9/2005 | Geser et al. | |
| 2005/0239778 A1 | 10/2005 | Konetzki et al. | |
| 2005/0247305 A1 | 11/2005 | Zierenberg et al. | |
| 2005/0250704 A1 | 11/2005 | Bassarab et al. | |
| 2005/0250705 A1 | 11/2005 | Bassarab et al. | |
| 2005/0255119 A1 | 11/2005 | Bassarab et al. | |
| 2005/0263618 A1 | 12/2005 | Spallek et al. | |
| 2005/0268909 A1 | 12/2005 | Bonney et al. | |
| 2005/0268915 A1 | 12/2005 | Wassenaar et al. | |
| 2005/0269359 A1 | 12/2005 | Raats | |
| 2006/0002863 A1 | 1/2006 | Schmelzer et al. | |
| 2006/0016449 A1 | 1/2006 | Eicher et al. | |
| 2006/0035874 A1 | 2/2006 | Lulla et al. | |
| 2006/0037612 A1 | 2/2006 | Herder et al. | |
| 2006/0067952 A1 | 3/2006 | Chen | |
| 2006/0086828 A1 | 4/2006 | Bougamont et al. | |
| 2006/0150971 A1 | 7/2006 | Lee et al. | |
| 2006/0196500 A1 | 9/2006 | Hochrainer et al. | |
| 2006/0225734 A1 | 10/2006 | Sagaser et al. | |
| 2006/0239886 A1 | 10/2006 | Nakayama et al. | |
| 2006/0239930 A1 | 10/2006 | Lamche et al. | |
| 2006/0254579 A1 | 11/2006 | Grychowski et al. | |
| 2006/0279588 A1 | 12/2006 | Yearworth et al. | |
| 2006/0282045 A1 | 12/2006 | Wilkinson et al. | |
| 2006/0285987 A1 | 12/2006 | Jaeger et al. | |
| 2006/0289002 A1 | 12/2006 | Hetzer et al. | |

(56) References Cited

U.S. PATENT DOCUMENTS

2006/0293293 A1 12/2006 Muller et al.
2007/0062518 A1 3/2007 Geser et al.
2007/0062519 A1 3/2007 Wuttke et al.
2007/0062979 A1 3/2007 Dunne
2007/0090205 A1 4/2007 Kunze et al.
2007/0090576 A1 4/2007 Geser et al.
2007/0107720 A1 5/2007 Boeck et al.
2007/0119449 A1 5/2007 Boehm et al.
2007/0137643 A1 6/2007 Bonney et al.
2007/0163574 A1 7/2007 Rohrschneider et al.
2007/0181526 A1* 8/2007 Frishman ............... B65D 41/42 215/257
2007/0183982 A1 8/2007 Berkel et al.
2007/0210121 A1 9/2007 Stadelhofer
2007/0221211 A1 9/2007 Sagalovich
2007/0264437 A1 11/2007 Zimmermann et al.
2007/0272763 A1 11/2007 Dunne et al.
2007/0298116 A1 12/2007 Bechtold-Peters et al.
2008/0017192 A1 1/2008 Southby et al.
2008/0029085 A1 2/2008 Lawrence et al.
2008/0060640 A1 3/2008 Waldner et al.
2008/0083408 A1 4/2008 Hodson et al.
2008/0092885 A1 4/2008 von Schuckmann
2008/0156321 A1 7/2008 Bowman et al.
2008/0163869 A1 7/2008 Nobutani et al.
2008/0197045 A1 8/2008 Metzger et al.
2008/0249459 A1 10/2008 Godfrey et al.
2008/0264412 A1 10/2008 Meyer et al.
2008/0265198 A1 10/2008 Warby
2008/0283553 A1 11/2008 Cox et al.
2008/0299049 A1 12/2008 Stangl
2008/0308580 A1 12/2008 Gaydos et al.
2009/0032427 A1 2/2009 Cheu et al.
2009/0060764 A1 3/2009 Mitzlaff et al.
2009/0075990 A1 3/2009 Schmidt
2009/0114215 A1 5/2009 Boeck et al.
2009/0166379 A1 7/2009 Wright et al.
2009/0170839 A1 7/2009 Schmidt
2009/0185983 A1 7/2009 Freund et al.
2009/0197841 A1 8/2009 Kreher et al.
2009/0202447 A1 8/2009 Kreher et al.
2009/0211576 A1 8/2009 Lehtonen et al.
2009/0221626 A1 9/2009 Schmidt
2009/0235924 A1 9/2009 Holakovsky et al.
2009/0272664 A1 11/2009 Marshall et al.
2009/0293870 A1 12/2009 Brunnberg et al.
2009/0306065 A1 12/2009 Schmidt
2009/0308772 A1 12/2009 Abrams
2009/0314287 A1 12/2009 Spallek et al.
2009/0317337 A1 12/2009 Schmidt
2010/0012120 A1 1/2010 Herder et al.
2010/0018524 A1 1/2010 Jinks et al.
2010/0018997 A1* 1/2010 Faneca Llesera ... B05B 11/0027 222/153.06
2010/0044393 A1 2/2010 Moretti
2010/0056559 A1 3/2010 Schmelzer et al.
2010/0084531 A1 4/2010 Schuchman
2010/0095957 A1 4/2010 Corbacho
2010/0144784 A1 6/2010 Schmelzer et al.
2010/0168710 A1 7/2010 Braithwaite
2010/0237102 A1* 9/2010 Margheritis ............. 222/153.06
2010/0242557 A1 9/2010 Spreitzer et al.
2010/0242954 A1 9/2010 Hahn et al.
2010/0313884 A1 12/2010 Elliman
2010/0331765 A1 12/2010 Sullivan et al.
2011/0005517 A1 1/2011 Boeck et al.
2011/0041842 A1 2/2011 Bradshaw et al.
2011/0168175 A1 7/2011 Dunne et al.
2011/0239594 A1 10/2011 Nottingham et al.
2011/0240679 A1* 10/2011 Langlos .............. B05B 11/3049 222/321.7
2011/0245780 A1 10/2011 Helmer et al.
2011/0268668 A1 11/2011 Lamche et al.
2011/0277753 A1 11/2011 Dunne et al.
2011/0290239 A1 12/2011 Bach et al.
2011/0290242 A1 12/2011 Bach et al.
2011/0290243 A1 12/2011 Bach et al.
2012/0090603 A1 4/2012 Dunne et al.
2012/0132199 A1 5/2012 Kiesewetter
2012/0138049 A1 6/2012 Wachtel
2012/0138713 A1 6/2012 Schuy et al.
2012/0260913 A1 10/2012 Bach et al.
2012/0325204 A1 12/2012 Holakovsky et al.
2013/0012908 A1* 1/2013 Yeung .................. A61J 1/1412 604/404
2013/0056888 A1 3/2013 Holakovsky et al.
2013/0125880 A1 5/2013 Holakovsky et al.
2013/0125881 A1 5/2013 Holakovsky et al.
2013/0126389 A1 5/2013 Holakovsky et al.
2013/0206136 A1 8/2013 Herrmann
2013/0269687 A1 10/2013 Besseler et al.
2014/0121234 A1 5/2014 Kreher et al.
2014/0190472 A1 7/2014 Holakovsky et al.
2014/0228397 A1 8/2014 Schmelzer et al.
2014/0331994 A1 11/2014 Holakovsky et al.
2015/0040890 A1 2/2015 Besseler et al.
2015/0040893 A1 2/2015 Besseler et al.
2015/0041558 A1 2/2015 Besseler et al.
2015/0114387 A1 4/2015 Bach et al.
2015/0122247 A1 5/2015 Besseler et al.
2015/0258021 A1 9/2015 Kreher et al.
2015/0306087 A1 10/2015 Schmelzer et al.
2015/0320947 A1 11/2015 Eicher et al.
2015/0320948 A1 11/2015 Eicher et al.
2016/0095992 A1 4/2016 Wachtel

FOREIGN PATENT DOCUMENTS

CA 2233981 A1 4/1997
CA 2237853 A1 6/1997
CA 2251828 A1 10/1997
CA 2275392 A1 7/1998
CA 2297174 A1 2/1999
CA 2343123 A1 4/2000
CA 2434872 A1 8/2002
CA 2497059 A1 3/2004
CA 2497680 A1 3/2004
CA 2513167 A1 10/2004
CA 2557020 A1 9/2005
CA 2653183 A1 12/2007
CA 2653422 A1 12/2007
CN 1125426 A 6/1996
CN 1849174 A 10/2006
CN 101247897 A 8/2008
DE 1653651 A1 7/1971
DE 2754100 A1 6/1978
DE 4117078 A1 11/1992
DE 19625027 A1 1/1997
DE 19615422 A1 11/1997
DE 19653969 A1 6/1998
DE 19902844 C1 11/1999
DE 10007591 A1 11/2000
DE 10104367 A1 8/2002
DE 10300983 A1 7/2004
DE 102004031673 A1 1/2006
DE 202006017793 U1 1/2007
DE 01102006025871 A1 12/2007
DK 83175 C 7/1957
DK 140801 B 11/1979
EP 0018609 A1 11/1980
EP 0289332 A1 11/1988
EP 0289336 A2 11/1988
EP 0354507 A2 2/1990
EP 0364235 A1 4/1990
EP 0372777 A2 6/1990
EP 0386800 A1 9/1990
EP 0412524 A1 2/1991
EP 0505123 A1 9/1992
EP 0520571 A1 12/1992
EP 0622311 A2 11/1994
EP 0642992 A2 3/1995
EP 0679443 A1 11/1995
EP 0735048 A1 10/1996
EP 0811430 A1 3/1997

(56) References Cited

FOREIGN PATENT DOCUMENTS

| | | | |
|---|---|---|---|
| EP | 0778221 | A1 | 6/1997 |
| EP | 0845253 | A2 | 6/1998 |
| EP | 0845265 | A1 | 6/1998 |
| EP | 0860210 | A2 | 8/1998 |
| EP | 0916428 | A2 | 5/1999 |
| EP | 0965355 | A2 | 12/1999 |
| EP | 0970751 | A2 | 1/2000 |
| EP | 1003478 | A1 | 5/2000 |
| EP | 1017469 | A1 | 7/2000 |
| EP | 1025923 | A1 | 8/2000 |
| EP | 1068906 | A2 | 1/2001 |
| EP | 1075875 | A2 | 2/2001 |
| EP | 1092447 | A2 | 4/2001 |
| EP | 1157689 | A1 | 11/2001 |
| EP | 1211628 | A2 | 6/2002 |
| EP | 1245244 | A2 | 10/2002 |
| EP | 1312418 | A2 | 5/2003 |
| EP | 1375385 | A2 | 1/2004 |
| EP | 1521609 | A2 | 4/2005 |
| EP | 1535643 | A1 | 6/2005 |
| EP | 1595564 | A1 | 11/2005 |
| EP | 1595822 | A1 | 11/2005 |
| EP | 1726324 | A1 | 11/2006 |
| EP | 1736193 | A1 | 12/2006 |
| EP | 1795221 | A1 | 6/2007 |
| EP | 1813548 | A1 | 8/2007 |
| EP | 2135632 | A1 | 12/2009 |
| ES | 2262348 | T3 | 11/2006 |
| FR | 2505688 | A1 | 11/1982 |
| FR | 2604363 | A1 | 4/1988 |
| FR | 2673608 | A1 | 9/1992 |
| FR | 2756502 | A1 | 6/1998 |
| GB | 1524431 | A | 9/1978 |
| GB | 2081396 | A | 2/1982 |
| GB | 2101020 | A | 1/1983 |
| GB | 2279273 | A | 1/1995 |
| GB | 2291135 | A | 1/1996 |
| GB | 2332372 | A | 6/1999 |
| GB | 2333129 | A | 7/1999 |
| GB | 2347870 | A | 9/2000 |
| GB | 2355252 | A | 4/2001 |
| GB | 2398253 | A | 8/2004 |
| GB | 0700839.4 | | 7/2008 |
| JP | S5684246 | A | 7/1981 |
| JP | H01288265 | A | 11/1989 |
| JP | H0228121 | A | 1/1990 |
| JP | H057246 | | 2/1993 |
| JP | H0553470 | A | 3/1993 |
| JP | H06312019 | A | 11/1994 |
| JP | H07118164 | A | 5/1995 |
| JP | H07118166 | A | 5/1995 |
| JP | 07323086 | A | 12/1995 |
| JP | H08277226 | A | 10/1996 |
| JP | H092442 | A | 1/1997 |
| JP | H0977073 | A | 3/1997 |
| JP | H09315953 | A | 12/1997 |
| JP | 2001518428 | A | 10/2001 |
| JP | 2001346878 | A | 12/2001 |
| JP | 2002504411 | A | 2/2002 |
| JP | 2002235940 | A | 8/2002 |
| JP | 2003511212 | A | 3/2003 |
| JP | 2003299717 | A | 10/2003 |
| JP | 2004502502 | A | 1/2004 |
| JP | 2004097617 | A | 4/2004 |
| JP | 2005511210 | A | 4/2005 |
| JP | 2005144459 | A | 6/2005 |
| JP | 2007517529 | A | 7/2007 |
| JP | 2007245144 | A | 9/2007 |
| JP | 2007534379 | A | 11/2007 |
| JP | 2008119489 | A | 5/2008 |
| JP | 2008541808 | A | 11/2008 |
| JP | 2010526620 | A | 8/2010 |
| JP | 2010540371 | A | 12/2010 |
| WO | 8100674 | A1 | 3/1981 |
| WO | 8200785 | A1 | 3/1982 |
| WO | 8300288 | A1 | 2/1983 |
| WO | 8303054 | A1 | 9/1983 |
| WO | 8605419 | A1 | 9/1986 |
| WO | 8706137 | A1 | 10/1987 |
| WO | 8803419 | A1 | 5/1988 |
| WO | 8900889 | A1 | 2/1989 |
| WO | 8900947 | A1 | 2/1989 |
| WO | 8902279 | A1 | 3/1989 |
| WO | 8903672 | A1 | 5/1989 |
| WO | 8903673 | A1 | 5/1989 |
| WO | 8905139 | A1 | 6/1989 |
| WO | 9009780 | A1 | 9/1990 |
| WO | 9009781 | A1 | 9/1990 |
| WO | 9114468 | A1 | 10/1991 |
| WO | 9206704 | A1 | 4/1992 |
| WO | 9217231 | A1 | 10/1992 |
| WO | 9221332 | A1 | 12/1992 |
| WO | 9222286 | | 12/1992 |
| WO | 9313737 | A1 | 7/1993 |
| WO | 9324164 | A1 | 12/1993 |
| WO | 9325321 | A1 | 12/1993 |
| WO | 9407607 | A1 | 4/1994 |
| WO | 9417822 | A1 | 8/1994 |
| WO | 9425371 | A1 | 11/1994 |
| WO | 9427653 | A2 | 12/1994 |
| WO | 9503034 | A1 | 2/1995 |
| WO | 9532015 | A1 | 11/1995 |
| WO | 9600050 | A1 | 1/1996 |
| WO | 9606011 | A2 | 2/1996 |
| WO | 9606581 | A1 | 3/1996 |
| WO | 9623522 | A1 | 8/1996 |
| WO | 9701329 | A1 | 1/1997 |
| WO | 9706813 | A1 | 2/1997 |
| WO | 9706842 | A1 | 2/1997 |
| WO | 9712683 | A1 | 4/1997 |
| WO | 9712687 | A1 | 4/1997 |
| WO | 9720590 | A1 | 6/1997 |
| WO | 9723208 | A1 | 7/1997 |
| WO | 9727804 | A1 | 8/1997 |
| WO | 9735562 | A1 | 10/1997 |
| WO | 9741833 | A1 | 11/1997 |
| WO | 9812511 | A2 | 3/1998 |
| WO | 9827959 | A2 | 7/1998 |
| WO | 9831346 | A1 | 7/1998 |
| WO | 9839043 | A1 | 9/1998 |
| WO | 9901227 | A1 | 1/1999 |
| WO | 9907340 | A1 | 2/1999 |
| WO | 9911563 | A1 | 3/1999 |
| WO | 9916530 | A1 | 4/1999 |
| WO | 9943571 | A1 | 9/1999 |
| WO | 9962495 | A2 | 12/1999 |
| WO | 9965464 | | 12/1999 |
| WO | 0001612 | A2 | 1/2000 |
| WO | 0023037 | A1 | 4/2000 |
| WO | 0023065 | A2 | 4/2000 |
| WO | 0027543 | A1 | 5/2000 |
| WO | 0033965 | A1 | 6/2000 |
| WO | 0037336 | A1 | 6/2000 |
| WO | 0049988 | A2 | 8/2000 |
| WO | 0064779 | A1 | 11/2000 |
| WO | 0113885 | A1 | 3/2001 |
| WO | 0128489 | A1 | 4/2001 |
| WO | 0164182 | A2 | 9/2001 |
| WO | 0185097 | A2 | 11/2001 |
| WO | 0187392 | A2 | 11/2001 |
| WO | 0197888 | A2 | 12/2001 |
| WO | 0198175 | A1 | 12/2001 |
| WO | 0198176 | A2 | 12/2001 |
| WO | 0204054 | A1 | 1/2002 |
| WO | 0205879 | A1 | 1/2002 |
| WO | 0217988 | A2 | 3/2002 |
| WO | 0232899 | A1 | 4/2002 |
| WO | 0234411 | A1 | 5/2002 |
| WO | 02070141 | A1 | 9/2002 |
| WO | 02089887 | A1 | 11/2002 |
| WO | 03002045 | A1 | 1/2003 |
| WO | 03014832 | A1 | 2/2003 |
| WO | 03020253 | A2 | 3/2003 |
| WO | 03022332 | A2 | 3/2003 |

(56) References Cited

FOREIGN PATENT DOCUMENTS

| | | | |
|---|---|---|---|
| WO | 03035030 | A1 | 5/2003 |
| WO | 03037159 | A2 | 5/2003 |
| WO | 03037259 | A2 | 5/2003 |
| WO | 03049786 | A2 | 6/2003 |
| WO | 03050031 | A1 | 6/2003 |
| WO | 03053350 | A2 | 7/2003 |
| WO | 03057593 | A1 | 7/2003 |
| WO | 03059547 | A1 | 7/2003 |
| WO | 03068299 | A1 | 8/2003 |
| WO | 03087097 | A1 | 10/2003 |
| WO | 03097139 | A1 | 11/2003 |
| WO | 2004019985 | A1 | 3/2004 |
| WO | 2004022052 | A1 | 3/2004 |
| WO | 2004022132 | A2 | 3/2004 |
| WO | 2004022244 | A1 | 3/2004 |
| WO | 2004024157 | A1 | 3/2004 |
| WO | 2004033954 | A2 | 4/2004 |
| WO | 2004062813 | A1 | 7/2004 |
| WO | 2004078236 | A2 | 9/2004 |
| WO | 2004089551 | A2 | 10/2004 |
| WO | 2004091704 | A1 | 10/2004 |
| WO | 2004098689 | A1 | 11/2004 |
| WO | 2004098795 | A1 | 11/2004 |
| WO | 2005000476 | A1 | 1/2005 |
| WO | 2005004844 | A1 | 1/2005 |
| WO | 2005014175 | A1 | 2/2005 |
| WO | 2005020953 | A1 | 3/2005 |
| WO | 2005030211 | A1 | 4/2005 |
| WO | 2005055976 | A2 | 6/2005 |
| WO | 2005077445 | A1 | 8/2005 |
| WO | 2005079997 | A1 | 9/2005 |
| WO | 2005080001 | A1 | 9/2005 |
| WO | 2005080002 | A1 | 9/2005 |
| WO | 2005087299 | A1 | 9/2005 |
| WO | 2005107837 | A1 | 11/2005 |
| WO | 2005109948 | A2 | 11/2005 |
| WO | 2005112892 | A1 | 12/2005 |
| WO | 2005112996 | A1 | 12/2005 |
| WO | 2005113007 | A2 | 12/2005 |
| WO | 2006011638 | A1 | 2/2006 |
| WO | 2006018392 | A1 | 2/2006 |
| WO | 2006027595 | A1 | 3/2006 |
| WO | 2006037636 | A2 | 4/2006 |
| WO | 2006037948 | A2 | 4/2006 |
| WO | 2006042297 | A2 | 4/2006 |
| WO | 2006045813 | A1 | 5/2006 |
| WO | 2006110080 | A1 | 10/2006 |
| WO | 2006125577 | A2 | 11/2006 |
| WO | 2006126014 | A2 | 11/2006 |
| WO | 2007011475 | A1 | 1/2007 |
| WO | 2007022898 | A2 | 3/2007 |
| WO | 2007030162 | A2 | 3/2007 |
| WO | 2007049239 | A2 | 5/2007 |
| WO | 2007060104 | A2 | 5/2007 |
| WO | 2007060105 | A1 | 5/2007 |
| WO | 2007060106 | A1 | 5/2007 |
| WO | 2007060107 | A1 | 5/2007 |
| WO | 2007060108 | A2 | 5/2007 |
| WO | 2007062721 | A1 | 6/2007 |
| WO | 2007090822 | A2 | 8/2007 |
| WO | 2007101557 | A2 | 9/2007 |
| WO | 2007128381 | A1 | 11/2007 |
| WO | 2007134965 | A1 | 11/2007 |
| WO | 2007134966 | A1 | 11/2007 |
| WO | 2007134967 | A1 | 11/2007 |
| WO | 2007134968 | A1 | 11/2007 |
| WO | 2007141201 | A1 | 12/2007 |
| WO | 2007141203 | A1 | 12/2007 |
| WO | 2008023017 | A2 | 2/2008 |
| WO | 2008047035 | A2 | 4/2008 |
| WO | 2008077623 | A1 | 7/2008 |
| WO | 2008124666 | A2 | 10/2008 |
| WO | 2008138936 | A2 | 11/2008 |
| WO | 2008146025 | A2 | 12/2008 |
| WO | 2009006137 | A1 | 1/2009 |
| WO | 2009047021 | A1 | 4/2009 |
| WO | 2009047173 | A2 | 4/2009 |
| WO | 2009050978 | A1 | 4/2009 |
| WO | 2009090245 | A1 | 7/2009 |
| WO | 2009103510 | A1 | 8/2009 |
| WO | 2009115200 | A1 | 9/2009 |
| WO | 2010005946 | A2 | 1/2010 |
| WO | 2010006870 | A1 | 1/2010 |
| WO | 2010094305 | A1 | 8/2010 |
| WO | 2010094413 | A2 | 8/2010 |
| WO | 2010112358 | A2 | 10/2010 |
| WO | 2010133294 | A2 | 11/2010 |
| WO | 2010149280 | A1 | 12/2010 |
| WO | 2011006711 | A1 | 1/2011 |
| WO | 2011064160 | A1 | 6/2011 |
| WO | 2011064163 | A1 | 6/2011 |
| WO | 2011064164 | A1 | 6/2011 |
| WO | 2011131779 | A1 | 10/2011 |
| WO | 2011154295 | A2 | 12/2011 |
| WO | 2011160932 | A1 | 12/2011 |
| WO | 2012130757 | A1 | 10/2012 |
| WO | 2012159914 | A1 | 11/2012 |
| WO | 2012160047 | A2 | 11/2012 |
| WO | 2012160052 | A1 | 11/2012 |
| WO | 2012161685 | A1 | 11/2012 |
| WO | 2012162305 | A1 | 11/2012 |
| WO | 2013017640 | A1 | 2/2013 |
| WO | 2013110601 | A1 | 8/2013 |
| WO | 2013152861 | A1 | 10/2013 |
| WO | 2013152894 | A1 | 10/2013 |
| WO | 2014111370 | A1 | 7/2014 |
| WO | 2015018901 | A1 | 2/2015 |
| WO | 2015018903 | A1 | 2/2015 |
| WO | 2015018904 | A1 | 2/2015 |
| WO | 2015169431 | A2 | 11/2015 |
| WO | 2015169732 | A1 | 11/2015 |
| ZA | 199901520 | A | 12/1999 |

OTHER PUBLICATIONS

"Activate". Collins English Dictionary, London: Collins, 2000, 2 pages. [Retrieved at http://search.credoreference.com/content/entry/hcengdict/activate/0 on Jun. 12, 2014].
"Lung Cancer". Merck Manual Home Edition, pp. 1-7. [Accessed at www.merck.com/mmhe/print/sec04/ch057/ch057a.html, on Jul. 28, 2010].
Abstract in English for DE19902844, 1999.
Abstract in English for DE4117078, 1992.
Abstract in English for EP0354507, 1990.
Abstract in English for FR2756502, 1998.
Abstract in English for JPS5684246, 1979.
Abstract in English of DE10007591, 2000.
Abstract in English of DE202006017793, 2007.
Abstract in English of FR2604363, Sep. 30, 1986.
Abstract in English of JPH0553470, 1993.
Abstract in English of JPH057246, 1993.
Abstract in English of JPH07118164, 1995.
Abstract in English of JPH07118166, 1995.
Abstract in English of JPH08277226,1996.
Abstract in English of JPH092442, 1997.
Abstract in English of JPH09315953, 1997.
Abstract in English of JPH0977073, 1997.
Abstract in English of WO199706813, 1997.
Abstract in English of WO199839043, 1998.
Abstract in English of WO2002070141, 2002.
Ackermann et al.; Quantitative Online Detection of Low-Concentrated Drugs via a SERS Microfluidic System; ChemPhysChem; 2007; vol. 8; No. 18; pp. 2665-2670.
Beasley R et al: "Preservatives in Nebulizer solutions: Risks without Benefit" Pharmacotherapy, Boston, US, Bd. 18, Nr. 1, Jan. 1998.
Beasley R et al: "Preservatives in Nebulizer solutions: Risks without Benefit" Pharmacotherapy, Boston, US, Bd. 18, Nr. 1, Jan. 1998, pp. 130-139.
Bocci et al., "Pulmonary catabolism of interferons: alveolar absorption of 125I-labeled human interferon alpha is accompanied by partial loss of biological activity". Antiviral Research, vol. 4, 1984, pp. 211-220.

(56) References Cited

OTHER PUBLICATIONS

Chen, F-K et al., "A study of forming pressure in the tube-hydroforming process". Journal of Materials Processing Technology, 192-193, 2007, p. 404-409.
China Suppliers, Shanghai Lite Chemical Technology Co., Ltd. Product details on polyvinylpyrrolidones. Obtained online by the USPTO examiner on Apr. 24, 2011.
Cras et al., "Comparison of chemical cleaning methods of glass in preparation for silanization". Biosensors & Bioelectronics, vol. 14, 1999, pp. 683-688.
Diamond et al., "Substance P Fails to Mimic Vagally Mediated Nonadrenergic Bronchodilation". Peptides, vol. 3, 1982, pp. 27-29.
Elwenspoek et al., "Silicon Micromachining", Chapter 3, Mechanical Microsensors, Springer-Verlag Berlin Heidelberg, 2001, 4 pages.
English Language Abstract of EP1068906, 2001.
Fuchs et al., "Neopterin, biochemistry and clinical use as a marker for cellular immune reactions". International Archives of Allergy and Immunology, vol. 101, No. 1, 1993, pp. 1-6, Abstract 1p.
Han et al.; Surface activation of thin silicon oxides by wet cleaning and silanization; Thin Solid Films; 2006; vol. 510; No. 1-2; pp. 175-180.
Henkel et al.; Chip modules for generation and manipulation of fluid segments for micro serial flow processes; Chemical Engineering Journal; 2004; vol. 101; pp. 439-445.
Hoffmann et al., "Mixed self-assembled monolayers (SAMs) consisting of methoxy-tri(ethylene glycol)-terminated and alkyl-terminated dimethylchlorosilanes control the non-specific adsorption of proteins at oxidic surfaces". Journal of Colloid and Interface Science, vol. 295, 2006, pp. 427-435.
Husseini et al., "Alkyl Monolayers on Silica Surfaces Prepared Using Neat, Heated Dimethylmonochlorosilanes with Low Vapor Pressures". Langmuir, vol. 19, 2003, pp. 5169-5171.
IP et al., "Stability of Recombinant Consensus Interferon to Air-Jet and Ultrasonic Nebulization". Journal of Pharmaceutical Sciences, vol. 84, No. 10, Oct. 1995, pp. 1210-1214.
Jendle et al., "Intrapulmonary administration of insulin to healthy volunteers". Journal of Internal Medicine, vol. 240, 1996, pp. 93-98.
JP2005144459—English language abstract only.
Kutchoukov et al., "Fabrication of nanofluidic devices using glass-to-glass anodic bonding" Sensors and Actuators A, vol. 114, 2004, pp. 521-527.
Lougheed et al., "Insulin Aggregation in Artificial Delivery Systems". Diabetologia, vol. 19, 1980, pp. 1-9.
Mandal et al., "Cytophobic surface modification of microfluidic arrays for in situ parallel peptide synthesis and cell adhesion assays". Biotechnology Progress, vol. 23, No. 4, 2007, pp. 972-978 (Author Manuscript Available in PMC, Sep. 21, 2009, 19 pages).
Niven et al., "Some Factors Associated with the Ultrasonic Nebulization of Proteins". Pharmaceutical Research, vol. 12, No. 1, 1995, pp. 53-59.
Remington Pharmacy, Editor Alfonso R. Gennaro. 19th ed., Spanish Secondary Edition: Panamericana, Spain, 1995, Sciarra, J.J., "Aerosols", pp. 2560-2582. The English translation is from the 1995 English Primary Edition, Sciarra, J.J., Chapter 95, R97-1185.
Trasch et al., "Performance data of refloquant Glucose in the Evaluation of Reflotron". Clinical Chemistry, vol. 30, 1984, p. 969 (abstract only).
Wall et al., "High levels of exopeptidase activity are present in rat and canine bronchoalveolar lavage fluid". International Journal of Pharmaceutics, vol. 97, Issue 1-3, pp. 171-181, 1993, Abstract pp. 1-2.
Wang et al.; Self-Assembled Silane Monolayers: Fabrication with Nanoscale Uniformity; Langmuir; 2005; vol. 21; No. 5; pp. 1848-1857.
Abstract in English for WO2009050978, 2009.
Abstract in English for JP2002-235940, 2001.

* cited by examiner

NEBULIZER

BACKGROUND

The present invention relates to a nebulizer.

The starting point for the present invention is a nebulizer as illustrated in WO 2006/125577 A2. The nebulizer has, as a reservoir for fluid which is to be atomized, an insertable rigid container having an inner bag containing the fluid and a pressure generator with a drive spring for delivering and atomizing the fluid. Preferably, the container is pre-installed in the nebulizer in the delivery state. Before being used for the first time a securing member of the nebulizer has to be opened or removed so that a housing of the nebulizer can be completely closed. Thus, the pre-installed container is opened by a delivery tube piercing a sealing and a septum to fluidically connect to the inner bag of the container. By rotating a lower housing part of the housing of the nebulizer the drive spring can be put under tension and fluid can be sucked into a compression chamber of the pressure generator. Simultaneously, the container is moved into the lower housing part in a stroke movement within the nebulizer and when tensioned for the first time the container may be pierced through its base by a piercing element in the lower housing part to allow venting of the container. After manual operation of a locking element the drive spring is released and the fluid in the pressure chamber is put under pressure by the drive spring and is delivered or atomized through a nozzle into a mouthpiece as an aerosol, without the use of propellant gas.

SUMMARY

Object of the present invention is to provide a nebulizer with optimized or facilitated handling.

According to one aspect of the present invention, the nebulizer comprises a securing member preventing fluidic connection or opening of the container in a delivery state. The container is already disposed in the nebulizer in the deli-very state, i.e. pre-installed. The securing member can be manually opened, removed, released or destroyed to allow fluidic connection or opening of the container, in particular before or for first use of the nebulizer. The securing member comprises an actuator to open, remove, release or destroy the securing member. This allows optimized and/or facilitated handling. In particular, it allows intuitive operation of the nebulizer. For example, a user will intuitively grab, tear, tilt, pull or push the actuator to open, remove, release or destroy the securing member and, then, completely close the nebulizer for using the nebulizer.

According to a further aspect of the present invention, the securing member comprises a pre-determined breaking line along which the securing member can be opened, in particular by pulling the actuator. This allows facilitated and/or optimized handling. In particular, it allows defined opening or removal of the securing member.

According to another aspect of the present invention, the securing member can be opened, released or destroyed by turning a (lower) housing part of the nebulizer relative to the housing or upper housing part of the nebulizer, i.e. by torsioning the securing member or a preferably sleeve-like body thereof. In particular, the securing member or body is opened along a pre-determined breaking line by this torsioning. This facilitates the handling.

According to a further aspect of the present invention, the securing member is made of one piece and/or such that it can be opened, removed, released or destroyed in one piece. This allows an optimized or facilitated handling.

Preferably, the nebulizer comprises a housing part that is connectable to a housing of the nebulizer in a non-detachable manner after inserting or pre-installing the container. According a further aspect of the present invention, the housing part can be pre-mounted in another position, preferably in another rotational position, on the nebulizer or its housing than in the delivery state such that the housing part can be detached for inserting the container. This pre-mounting allows to re-open the nebulizer or its housing for inserting the container. Thus, the container can be inserted or pre-installed after producing the nebulizer. This allows optimized or facilitated handling.

The above aspects of the present invention and other aspects of the present invention as described the following can be realized independently from each other or in any combination.

A basic idea of the present invention is that even in its delivered state the nebulizer has a closed container provided therein and the nebulizer is constructed so that the container is opened inside the nebulizer before or during the first use of the nebulizer. This basic idea is called in the present invention also “pre-installed container”. This makes operation easier as there is no need to open the nebulizer, insert the container and close the nebulizer. Moreover, undesirable soiling or damage to the nebulizer caused by incorrect handling of the end-user when inserting the container can thus be prevented. Accordingly, there is better operational safety as it is impossible for the container to be wrongly inserted or otherwise misused during insertion.

Preferably, the container is not replaceable and in particular cannot be removed. This again leads to easier operation and hence improved operational reliability. This also prevents the nebulizer from being used or re-used in an undesirable or unauthorized manner.

In particular, the nebulizer cannot be opened and a lower housing part cannot be removed in order to replace the empty container with a full one in an undesirable manner.

The combination of the pre-installed container and the construction which makes the container non-replaceable results in particularly easy operation and high operational reliability as the user can only use the nebulizer as a single-use item until the container is empty, and undesirable or unauthorized further use of the nebulizer is prevented by the fact that the container cannot be replaced.

However, correspondingly easy operation and improved operational reliability for the user can also be achieved if the container is pre-installed at the pharmacy, for example, i.e. by trained staff, and optionally opened at the same time provided that the container is made non-exchangeable, in particular the nebulizer cannot be opened by the user (end-user).

DESCRIPTION OF THE DRAWINGS

Further advantages, features, characteristics and aspects of the present invention will become apparent from the claims and the following description of preferred embodiments with reference to the drawings. It shows:

DETAILED DESCRIPTION

Figure 1:
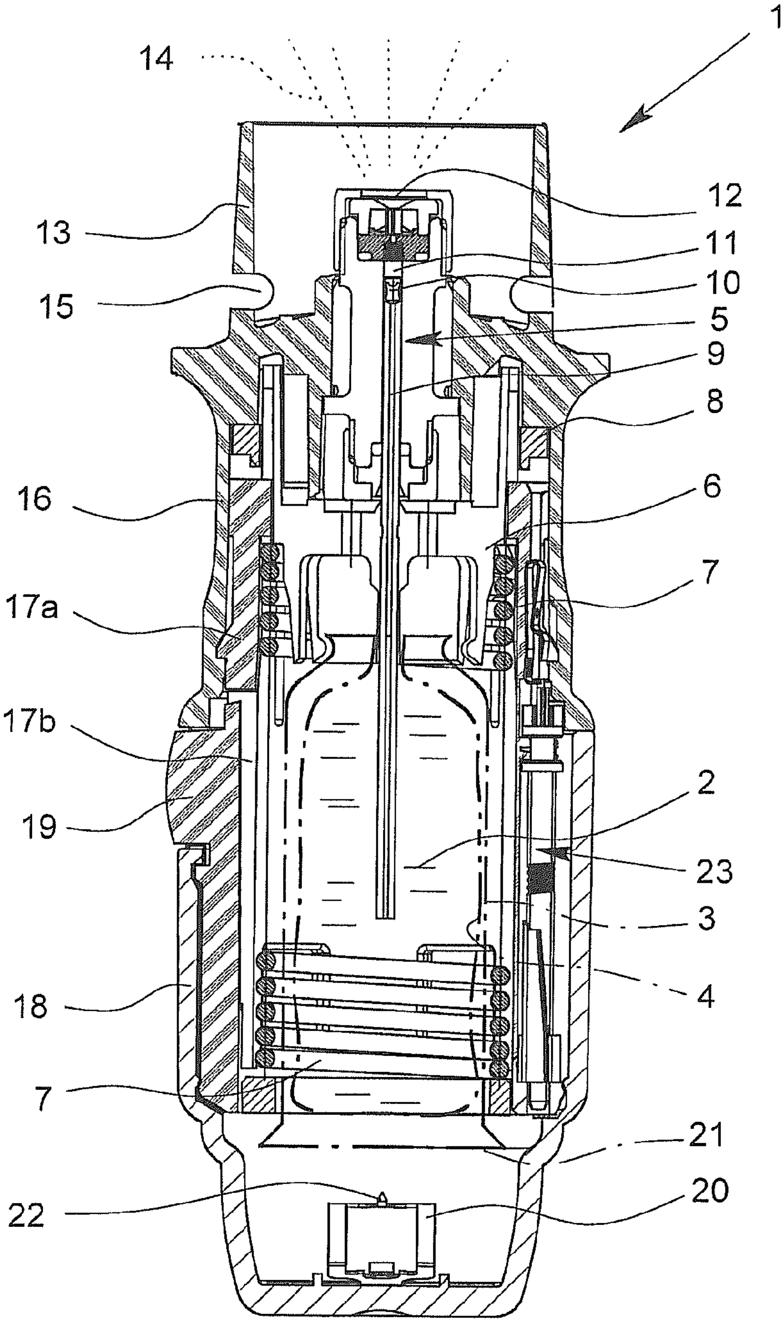
FIG. 1 a schematic section of a known nebulizer in a non-tensioned state.

In the Figures, the same reference numerals have been used for identical or similar parts, resulting in corresponding or comparable properties and advantages, even if the associated description is not repeated.

Figure 2:
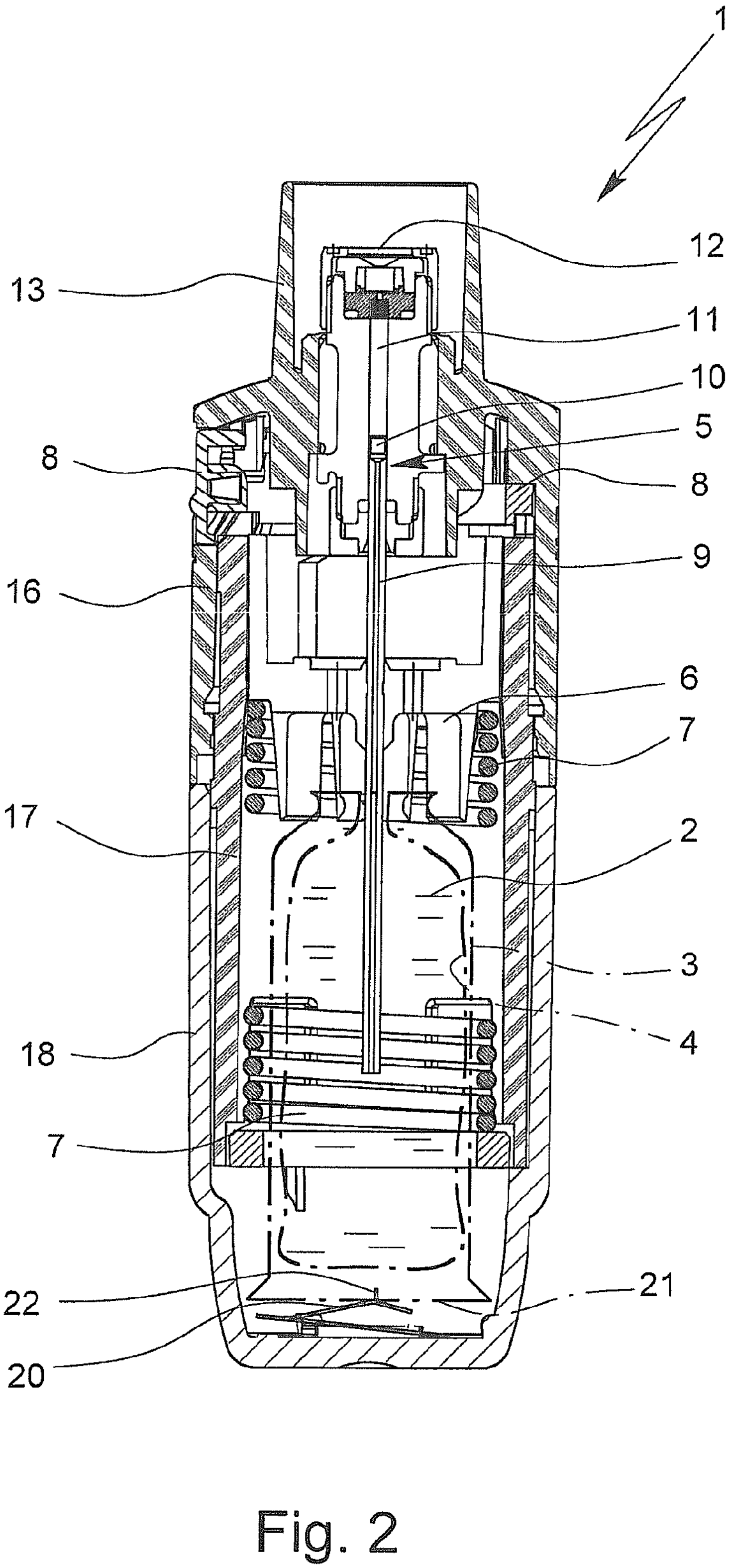
FIG. 2 a schematic section, rotated through 90° compared with FIG. 1, of the known nebulizer in a tensioned state.

FIGS. 1 and 2 show a known nebulizer 1 for atomizing a fluid 2, particularly a highly effective pharmaceutical composition, medicament or the like, dia-grammatically shown in a non-tensioned state (FIG. 1) and in a tensioned state (FIG. 2). The nebulizer 1 is constructed in particular as a portable inhaler and preferably operates only mechanical and/or without propellant gas.

When the fluid 2, preferably a liquid, more particularly a pharmaceutical composition, is nebulized, an aerosol 14 (FIG. 1) is formed, which can be breathed in or inhaled by a user. Usually the inhaling is done at least once a day, more particularly several times a day, preferably at set intervals, depending on the complain or illness from which the patient is suffering.

The nebulizer 1 is provided with or comprises an insertable container 3 containing the fluid 2. The container 3 thus forms a reservoir for the fluid 2 which is to be nebulized. Preferably, the container 3 contains an amount of fluid 2 or active substance which is sufficient to provide up to 200 dosage units, for example, i.e. to allow up to 200 sprays or applications. A typical container 3, as disclosed in WO 96/0601 1 A1, holds e.g. a volume of about 2 to 10 ml.

The container 3 is substantially cylindrical or cartridge-shaped and once the nebulizer 1 has been opened the container can be inserted therein from below and changed if desired. It is preferably of rigid construction, the fluid 2 in particular being held in a collapsible bag 4 in the container 3.

The nebulizer 1 comprises preferably a pressure generator 5 for conveying and nebulizing the fluid 2, particularly in a preset and optionally adjustable dosage amount. The pressure generator 5 comprises preferably a holder 6 for the container 3, an associated drive spring 7, only partly shown, a releasing element 8 which can be manually operated to release the spring 7, a conveying element, such as a conveying tube 9, a non-return valve 10, a pressure chamber 1 1 and/or an nozzle 12 for nebulizing the fluid 2 into a mouthpiece 13. The container 3 is fixed or held in the nebulizer 1 via the holder 6 such that the conveying tube 9 penetrates into the container 3. The holder 6 may be constructed so that the container 3 can be exchanged.

As the drive spring 7 is axially tensioned the holder 6 with the container 3 and the conveying tube 9 is moved downwards in the drawings and fluid 2 is sucked out of the container 3 into the pressure chamber 11 of the pressure generator 5 through the non-return valve 10. Then, the nebulizer 1 is in the so called activated or tensioned state.

During the subsequent relaxation after actuation of the releasing element 8 the fluid 2 in the pressure chamber 11 is put under pressure as the conveying tube 9 with its now closed non-return valve 10 is moved back upwards by the relaxation of the drive spring 7 and now acts as a pressing ram or piston. This pressure forces the fluid 2 through the nozzle 12, whereupon it is nebulized into the aerosol 14, as shown in FIG. 1. The preferred droplet size of the particles has already been discussed above in the introductory part.

Generally, the nebulizer 1 operates with a spring pressure of 5 to 200 MPa, preferably 10 to 100 MPa on the fluid 2, with a volume of fluid 2 delivered per stroke of 10 to 50 μ ï, preferably 10 to 20 μï, most preferably about 15 μï. The fluid 2 is converted into or nebulized as aerosol 14 the droplets of which have an aerodynamic diameter of up to 20 μηι, preferably 3 to 10 μηι. Preferably, the generated jet spray has an angle of 20° to 160°, preferably 80° to 100°. These values also apply to the nebulizer 1 according to the teaching of the present invention as particularly preferred values.

A user (not shown) can inhale the aerosol 14, while an air supply can be sucked into the mouthpiece 13 through at least one air supply opening 15.

Preferably, the nebulizer 1 or drive spring 7 can be manually activated or tensioned. The nebulizer 1 comprises preferably an upper housing part 16 and an inner part 17 which is rotatable relative thereto (FIG. 2) having an upper part 17*a* and a lower part 17*b* (FIG. 1), in particular a manually operable (lower) housing part 18 is releasable fixed, particularly fitted onto the inner part 17, preferably by means of a retaining element 19. Preferably, the housing parts 16 and 18 form a housing of the nebulizer 1. In order to insert and/or replace the container 3 the housing part 18 can be detached from the nebulizer 1 or its housing.

The housing part 18 can be rotated relative to the upper housing part 16, carrying with it the part 17*b* of the inner part 17. As a result the drive spring 7 is tensioned in the axial direction by means of a gear or transmission (not shown) acting on the holder 6. During tensioning the container 3 is moved axially downwards until the container 3 assumes an end position as shown in FIG. 2. In this activated or tensioned state the drive spring 7 is under tension.

During the nebulizing process the container 3 is moved back into its original position (non-tensioned position or state shown in FIG. 1) by the drive spring 7. Thus the container 3 executes a lifting or stroke movement during the tensioning process and during the atomizing process.

The housing part 18 preferably forms a cap-like lower housing part and fits around or over a lower free end portion of the container 3. As the drive spring 7 is tensioned the container 3 moves with its end portion (further) into the housing part 18 or towards the end face thereof, while an aeration means, such as an axially acting spring 20 arranged in the housing part 18, comes in contact with base 21 of the container 3 and pierces the container 3 or a base seal thereon with a piercing element 22 when the container 3 makes contact with it for the first time, to allow air in or aeration.

The nebulizer 1 may comprise a monitoring device 23 which counts the actuations of the nebulizer 1, preferably by detecting the rotation of the inner part 17 relative to the upper part 16 of the housing. Preferably, the monitoring device 23 blocks the actuation or use of the nebulizer 1, e.g. blocks the actuation of a releasing element 8, when a certain number of actuations or discharged doses has been reached or exceeded.

A preferred construction and mode of operation of a proposed inhaler or nebulizer 1 will now be described in more detail with reference to FIGS. 3 to 5, but emphasizing only essential differences from the nebulizer 1 according to FIGS. 1 and 2. The remarks relating to FIGS. 1 and 2 thus apply preferably accordingly or in a similar manner, while any desired combinations of features of the nebulizer 1 according to FIGS. 1 and 2 and the nebulizer 1 described below are possible.

Preferably, the container 3 is pre-installed. This can be realized in particular as shown in WO 2006/125577 A2 or as described in the following.

Figure 3:
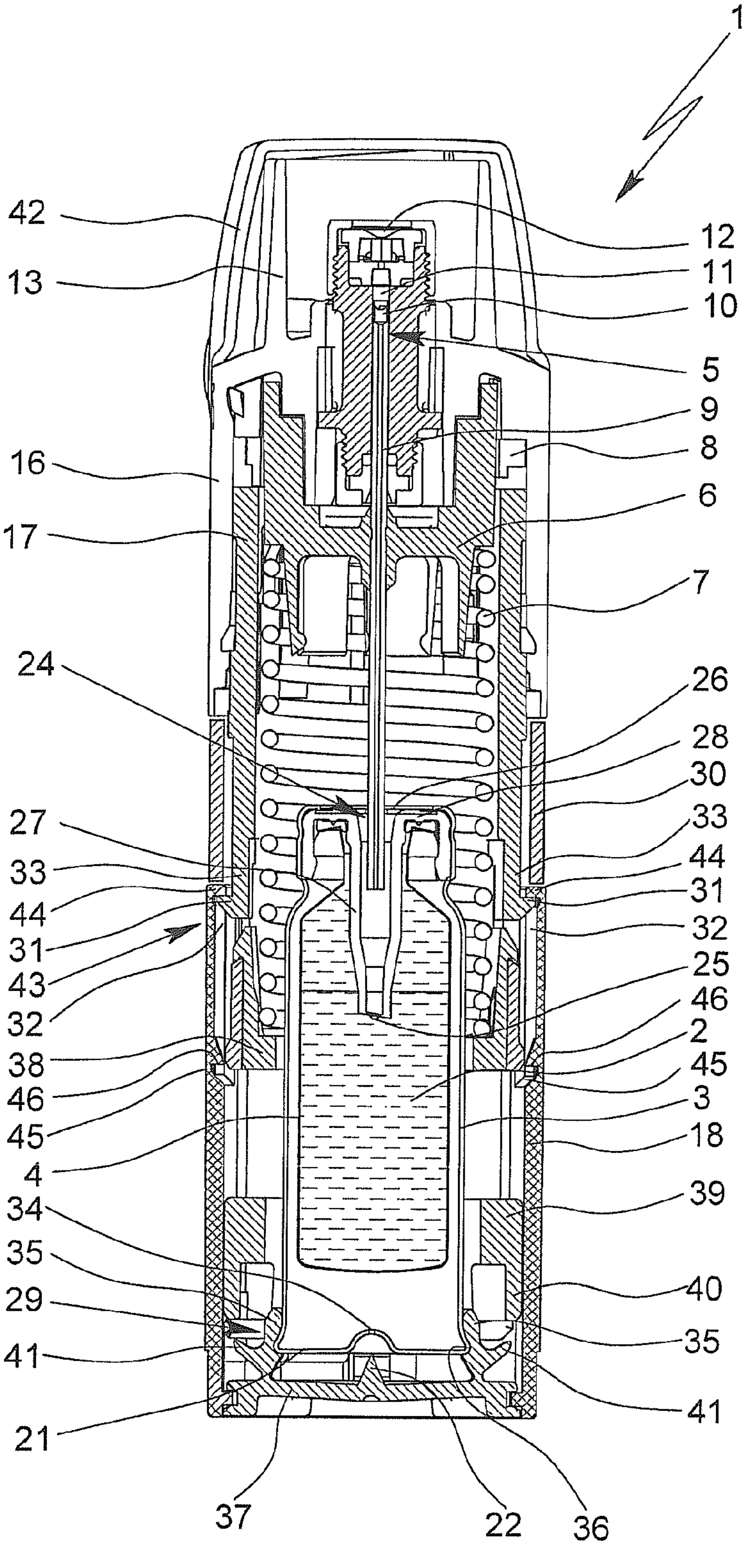
FIG. 3 a schematic section of a nebulizer according to the present invention in a delivery state with a partly closed housing and with a pre-installed, closed container.
Figure 4:
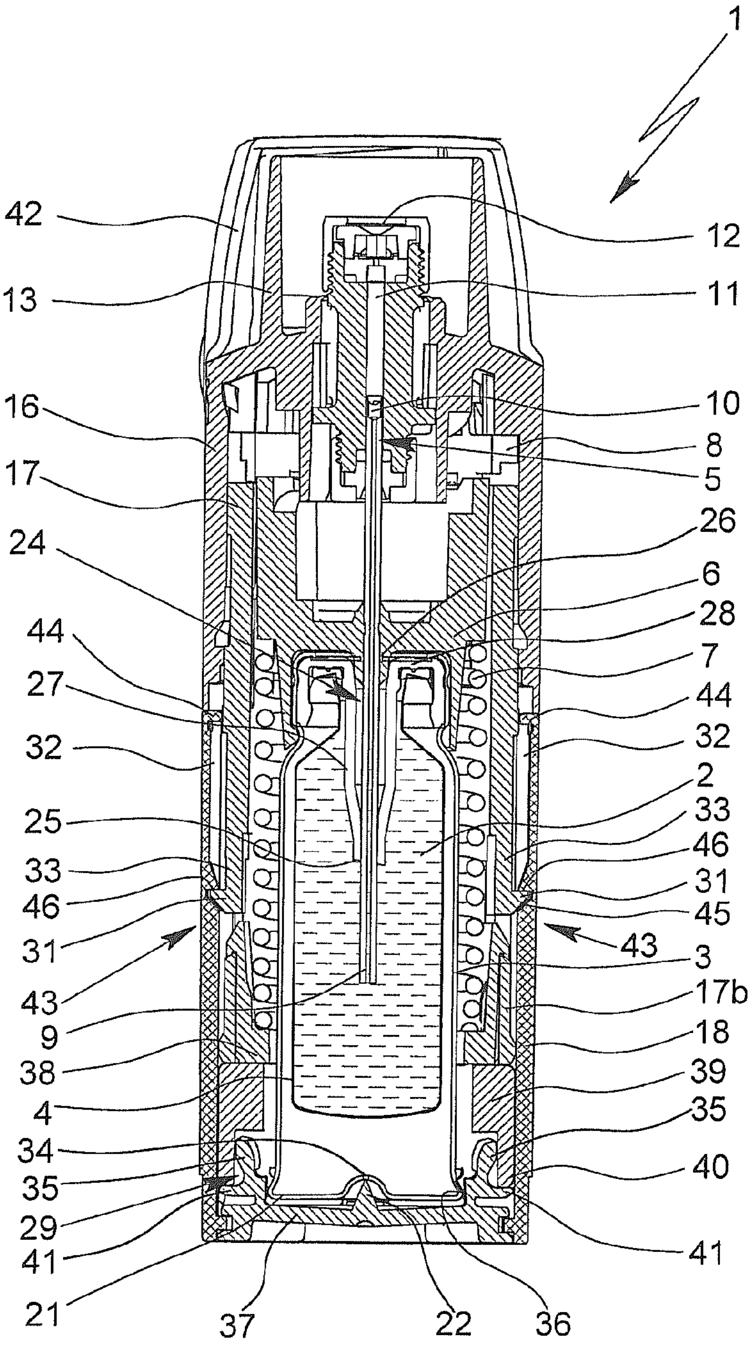
FIG. 4 a schematic section of the nebulizer according to FIG. 3 in an activated or tensioned state with the completely closed housing and with the opened container.
Figure 5:
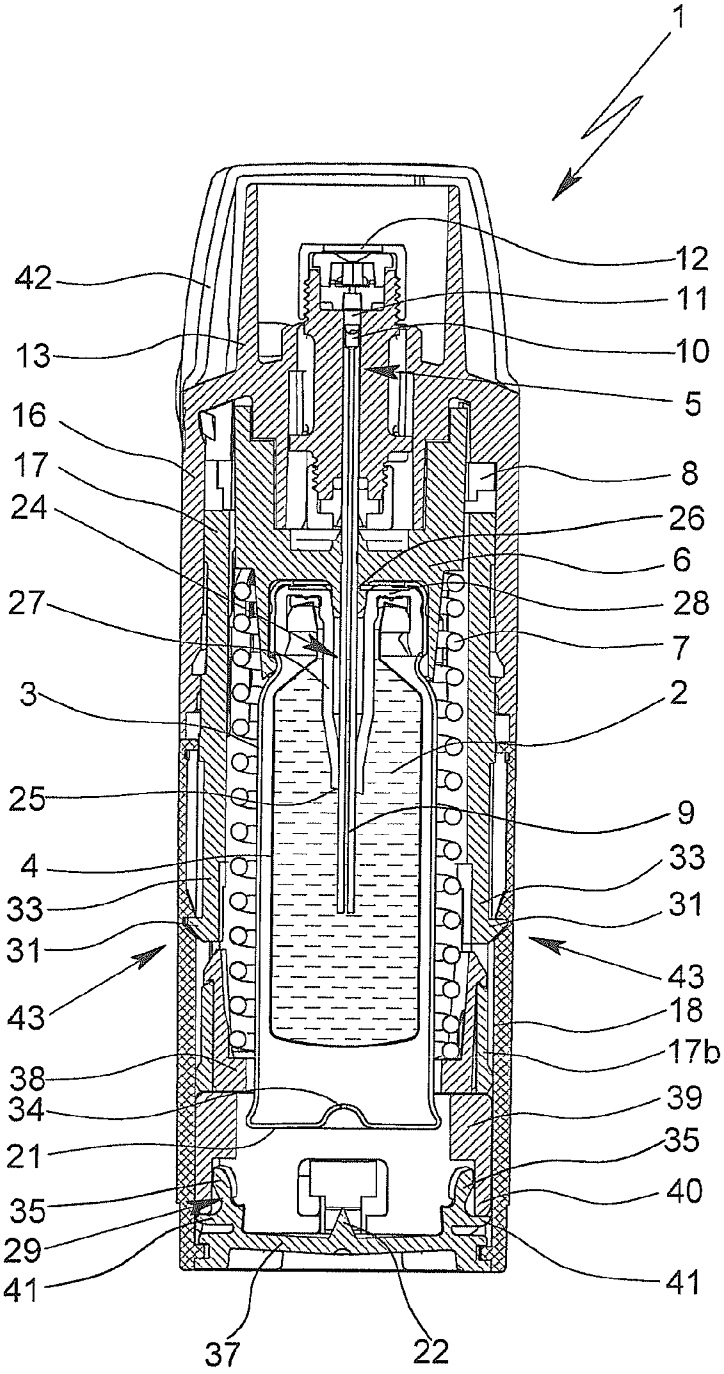
FIG. 5 a schematic section of the nebulizer according to FIG. 4 in a non-tensioned state.

FIGS. 3 to 5 shows, in schematic sectional views, a nebulizer 1 according to a preferred embodiment of the present invention. FIG. 3 shows the nebulizer 1 in a delivery state, i.e. with pre-installed container 3 which is still closed. In this state, the housing of the nebulizer 1 is not completely closed, in particular the housing part 18 is not completely pushed on the inner part 17. FIGS. 4 and 5 show the nebulizer 1 in an activated state with the housing completely closed and with the container 3 opened. In FIG. 4, the nebulizer 1 or drive spring 7 is tensioned, i. e. the container 3 is in its lower position. FIG. 5 shows the nebulizer 1 in a non-tensioned state, e.g. after the delivery or discharge of one dose of the fluid 2, the container 3 is in its upper position.

The container 3 is already mounted or pre-installed in the nebulizer 1 in the delivery state, as shown in FIG. 3. In this state, the container 3 is still closed, i.e. there is no fluidic connection between the container 3 or its bag 4 on one hand and the nebulizer 1 or its pressure generator 5 or the conveying element on the other hand.

The container 3 comprises a fluid outlet 24 for outputting the fluid 2 to be dispensed. In particular, the fluid outlet 24 allows a fluidic connection between the container 3 or its bag 4 on one hand and the nebulizer 1, its pressure generator 5 or the conveying element on the other hand.

In the non-installed state of the container 3, i.e. before mounting or pre-installation of the container 3 in the nebulizer 1, the fluid outlet 24 is closed by a first or inner closure 25 and optionally by a second or outer closure 26. In particular, the second closure 26 covers the first closure 25.

The first or inner closure 25 is preferably formed by a septum, a membrane, a plastic seal or the like and/or is provided inside the container 3.

In the preferred embodiment, the second closure 26 is preferably formed by a seal, a foil, a cap or the like, in particular by a metallic and/or composite foil or the like, which is preferably hot-sealed or attached in any other suitable manner on or to a head end or axial end of the container 3. In the shown embodiment, the second closure 26 is formed preferably by a hot-sealed foil with an aluminum layer.

Preferably, the closures 25 and 26 are designed such that separate opening is possible, in particular such that the second closure 26 can be opened indepen-dently from the first closure 25 and/or has to be opened before the first closure 25.

Preferably, the closures 25 and 26 are designed such that successive opening is possible by means of one common element, in particular the conveying element or conveying tube 9 or the like, and/or by piercing.

In the preferred embodiment, the first closure 25 and second closure 26 are arranged one after the other and/or spaced in axial direction or direction of the stroke movement of the container 3 or with respect to the main outlet direction of the fluid 2.

Preferably, the first or inner closure 25 is formed or supported by a closure part 27 extending from the outlet or head end of the container 3 into the container 3 or bag 4. The second or outer closure 26 is preferably located adjacent to the head or axial end of the container 3 and/or held or connected to a flange 28, which can be formed by the closure part 27 or any other suitable part. However, other constructional solutions are possible.

In the delivery state according to FIG. 3, the container 3 has been pre-installed, i.e. inserted into the nebulizer 1. However, the container 3 or its fluid outlet 24 is not yet opened. In particular, the second closure 26 is already opened, but not the first closure 25. This is achieved in particular in that the housing of the nebulizer 1 is closed only partly, i.e. not completely, in the delivery state, preferably by not completely closing or pushing on the housing part 18 in the shown embodiment. Preferably, the housing part 18 is snapped on or inserted only partly in the delivery state.

Generally, the container 3, fluid outlet 24 or closures 25 or 26 are opened in particular by means of a conveying element, such as the conveying tube 9, or the like and/or by piercing or in any other suitable manner. In particular, the opening is achieved by moving the container 3 relative to the nebulizer 1 or conveying element or tube 9 or the like and/or by movement in longitudinal or axial direction.

According to the present invention, the second closure 26 is already opened in the delivery state, preferably automatically by the nebulizer 1. In particular, the second closure 26 is opened during or by or when inserting the container 3 and/or during, by or when—preferably partly—closing the housing or housing part 18 of the nebulizer 1. Preferably, the first closure 25 is designed such that, when the conveying element pierces or opens the first closure 25, such as a septum, any material may not fall into the fluid 2, but will stay connected to the closure part 27 or the like and/or will be pivoted aside.

In particular, the container 3 is attached to or held by or secured in the housing part 18, in particular by a transportation lock 29, which is preferably arranged within or at the housing part 18. The transportation lock 29 holds the container 3 preferably temporarily, in particular before attaching the housing part 18 to the nebulizer 1 and/or in the delivery state. In particular, the transportation lock 29 holds the container fixed during the fluidic connection of container 3 and/or during the mechanic of container 3, here with holder 6.

Preferably, the second closure 26 is automatically opened, in particular pierced, when pre-installing the container 3 and/or attaching the housing part 18 to the nebulizer 1, in particular when snapping or pushing the housing part 18 partly on the nebulizer 1. Then, the opening or piercing is effected in the preferred embodiment by the conveying element or conveying tube 9 which extends in the delivery state through the second closure 26 and in particular into the closure part 27, i.e. partly into the container 3. Thus, a very compact arrangement and a small size or axial extension of the nebulizer 1 can be achieved in the delivery state. In particular, the housing part 18 can be snapped or pushed on or inserted into the nebulizer 1 or its housing in the delivery state significantly further than in case of the prior art.

In the delivery state, the first closure 25 and, thus the container 3 and the fluid outlet 24 remain closed.

In the delivery state, the nebulizer 1 or the housing part 18 is preferably secured, in particular by means of a securing means or member 30, such that the container 3 and/or housing part 18 are held sufficiently spaced from the nebulizer 1 or upper housing part 16 and/or prevented from being completely inserted or pushed on the conveying element or tube 9, the housing or inner housing part 17 or the like and/or such that (complete) opening of the container 3, namely of the first closure 25, is prevented.

In the shown embodiment, the securing means or member 30 is preferably mounted between the housing part 18 and the upper housing part 16 and preferably engages with or between the housing parts 16 and 18, so that the housing part or lower part 18 is axially secured or is kept or held sufficiently away or spaced from the upper housing part 16 to be able to hold the (still) closed container 3 or first closure 25 away from the conveying tube 9.

In the preferred embodiment, the securing member 30 is at least substantially hollow and/or cylindrical and is disposed axially between the (lower) housing part 18 and the upper housing part 16. To activate the nebulizer 1 or prepare its for use, i.e. to push the housing part 18 fully on in the axial direction and thereby open the container 3, the securing member 30 first has to be removed or released or opened.

In the shown preferred embodiment, the securing member 30 is constructed in the manner of a banderole or the like, made of plastics, for example, and/or can be manually opened, removed or destroyed. The securing member 30 may alternatively or simultaneously form or constitute a seal of origin. However, other embodiments of the securing member 30 are also possible, e.g. in the form of a security tag or the like.

Figure 6:
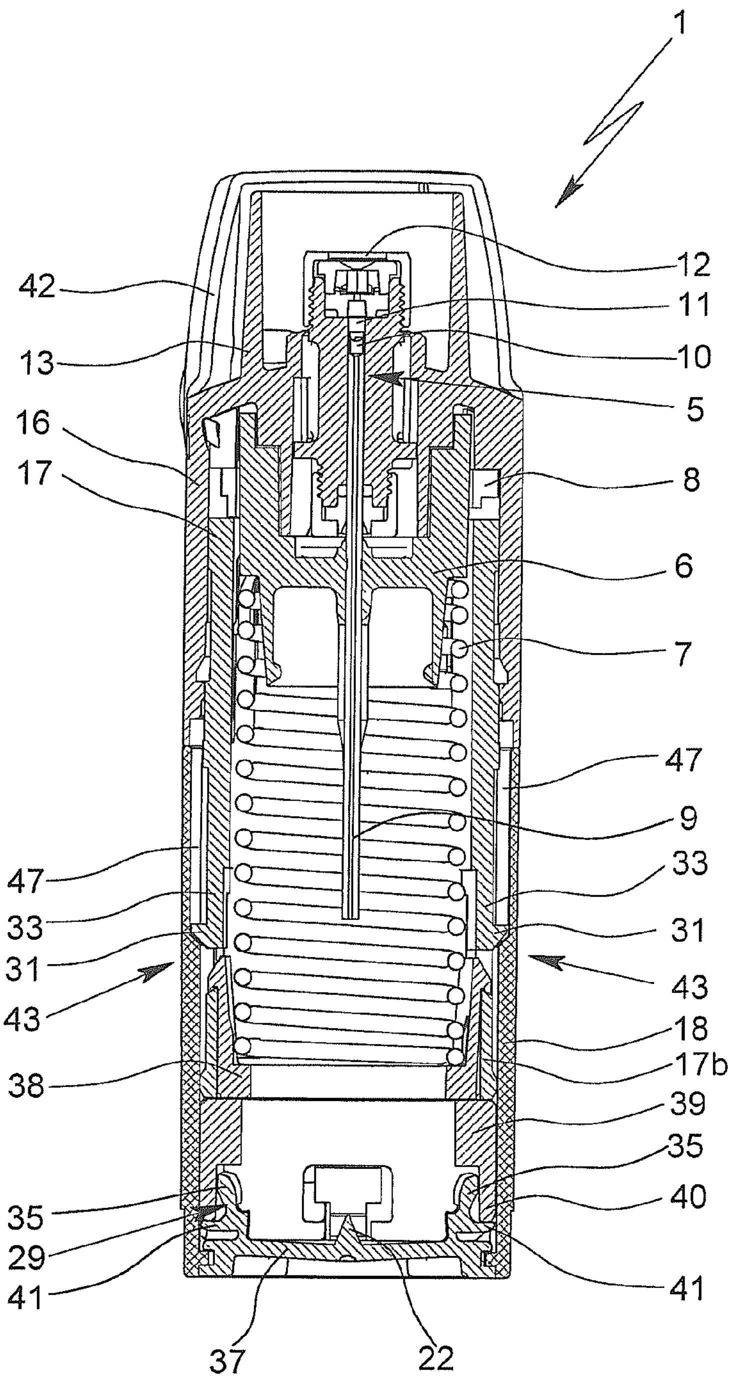
FIG. 6 a schematic section of the nebulizer similar to FIG. 5, but in a pre-mounted state without container.

The securing member 30 can be made of any suitable material, in particular of plastics, any composite or the like. Further, the securing member 30 can be made of paper, in particular like a paper sleeve as shown in FIG. 6. Alternatively or additionally, the securing member 31 can be formed by a label, tap, tag or tape and/or be self-adhesive. In this case, also a sleeve can be formed as shown in FIG. 3.

Further, examples will be explained later.

Preferably, the container 3 and/or housing part 18 are held positively or in a form-fit or interlocking manner in the delivery state. This is achieved in the preferred embodiment in particular by means of the transportation lock 29 acting between the container 3 and the housing part 18, and the securing means or member 30 acting between the housing part 18 and the housing of the nebulizer 1 or the upper housing part 16 or the like. However, the transportation lock 29 or securing means or member 30 could also act directly between the container 3 on one hand and the nebulizer 1, its housing, the upper housing part 16, the inner housing part 17 or the holder 6 on the other hand.

The pre-installed container 3, i.e. its first closure 25, is still closed in the delivery state, i.e. non-activated state with pre-installed container 3. In this non-activated position, the housing part 18 is preferably secured so that it cannot be lost and, in particular, cannot be released. Then, the housing part or lower part 18 of the nebulizer 1 can no longer be detached from the nebulizer 1 after it has been (partially) axially pushed on for the first time, i.e. the nebulizer 1 cannot be opened any longer, with the result that that the container 3 cannot be changed, i.e. cannot be removed again.

In order to secure the housing part 18, it is preferably held or latched positively or in an interlocking or form-fit manner. Preferably, the housing part 18 is secured by latching means 43 particularly comprising at least one latching lug 31, protrusion, nose or the like which engages in an associated latching recess 32 in the housing part 18 or the like and, thereby, secures the housing part 18 against axial removal by interlocking engagement. In the present embodiment, the latching lug 31 may be formed by or at a latching arm 33 which can preferably flex. Thus, a ratchet-like—or vice versa—latching means 43 for securing the housing part 18 to the nebulizer 1 or to its housing or the upper housing part 16 is formed. However, other constructional solutions are also possible.

Once the securing member 30 has been removed a user (not shown) can push the housing part 18 fully on in the axial direction and thereby open the container 3, i.e. first closure 25, by inserting the conveying element or conveying tube 9. FIGS. 4 and 5 show this activated state with the housing part 18 pushed fully on and/or the container 3 open (fluidically connected to the nebulizer 1 or its pressure generator 5 or the conveying element or tube 9). In this pushed on or activated state, the housing part 18 is preferably secured or axially fixed again by interlocking engagement, i.e. form-fit manner in axial direction, particularly by further engagement of the latching means 43 or by means of some other mechanical securing device.

FIG. 4 shows the nebulizer 1 or container 3 in the activated state, the container 3, i.e. first closure 25, is open, i.e. the container 3 or its fluid 2 is fluidically connected to the nebulizer 1 or its pressure generator 5, and the housing part 18 has been pushed fully on in the axial direction. In order to bring the holder 6 into (complete) engagement with the container 3 at the head end and then be able to move the container 3 back and/or forth for the suction/tensioning and pressing strokes, it may be necessary to tension the nebulizer 1 or it drive spring 7 for the first time. During this tensioning process the holder 6 is moved together with the conveying tube 9 axially towards or into the housing part 18, thus bringing the holder 6 into (complete) engagement with the container 3 and preferably also moving or pressing the container 3 against the piercing element 22 in the region of the base of the housing part 18 and thereby piercing or opening a vent opening 34 in the container base 21. FIG. 4 shows the nebulizer 1 in this tensioned and activated state. The holder 6 is engaged with the container 3 and the conveying tube 9 has been fully inserted into the container 3.

FIG. 5 shows the nebulizer 1 in the relaxed, non-tensioned state, i.e. after ato-mization or discharge of a dose of the fluid 2. The holder 6 and the container 3 are in the upper position. The holder 6 is still engaged with the container 3 and remains engaged during the further uses of the nebulizer 1. Further, the container 3 is still open and fluidically connected, i.e. the nebulizer 1 remains activated.

In the delivery state shown in FIG. 3, i.e. with the container 3, namely the first closure 25, (still) closed, the nebulizer 1 can be shipped or delivered to the user. Then, the user can store the nebulizer 1 with the pre-installed container 3. The container 3 will be opened later before or during the first use of the nebulizer 1, namely when removing the securing member 30 and completely closing the nebulizer 1 or housing or housing part 18.

It should be noted that the opening of the container 3 is preferably carried out exclusively by mechanical means and/or manual actuation. However, it is additionally or alternatively possible to open it in other ways, e.g. by chemical, electrical, magnetic, pneumatic, hydraulic or similar means.

The proposed nebulizer 1 is activated after the removal of the securing member 30 and (total) axial pushing on of the housing part 18 and can be used in the same way as the nebulizer 1 shown in FIGS. 1 and 2. The pre-installation of the container 3 prevents the wrong container 3 or used containers 3 from being inserted in the nebulizer 1 by the user. Additionally it ensures that a separately supplied container 3 is not accidentally opened before being inserted in the nebulizer 1. Additionally the proposed solution prevents possible soiling or damage to the nebulizer 1, e.g. the conveying tube 9 or the like, when the nebulizer 1 is opened and the container 3 is used improperly.

As preferably the container 3 cannot then be removed, especially because the nebulizer 1 cannot be opened and the housing part 18 cannot be removed again, undesirable replacement of the container 3 by the user and in particular undesirable interim or subsequent opening of the nebulizer 1 by the user can be prevented.

To prevent unwanted opening of the container 3, particularly of the first closure 25, in the delivery state of the nebulizer 1, preferably the transportation lock 29 is provided. By frictional, forcible or interlocking engagement, for example, the transportation lock 29 prevents the container 3 from undesirably moving axially in the nebulizer 1, e.g. during transportation, in the event of accidental dropping of the nebulizer 1 or the like.

In the following, a preferred realization of the transportation lock 29 will be explained. It has to be noted that the transportation lock 29 can be realized independently from the preferred partial opening or piercing of the container 3 in the delivery state, in particular namely opening of the second closure 26. In particular, the proposed function and construction of the transportation lock 29 can be realized independently from the features of the present claims.

In the preferred embodiment, the transportation lock 29 comprises at least one gripping arm 35, preferably a plurality of gripping arms 35, for axially holding the container 3 in the delivery state, in particular by (radially) engaging around its preferably radially expanded base 21 or edge 36, as shown in FIG. 3.

The gripping arms 35 are preferably held or formed by or attached to or molded unitary with a member 37 which may form the bottom or base or end face of the housing part 18. Preferably, the member 37 or bottom holds the gripping arms 35 such that the arms 35 can flex or pivot.

Preferably, the piercing element 22 is also formed by or held by the member 37.

It has to be noted that the member 37 and/or the transportation lock 29 may be inserted into the housing part 18. The transportation lock 29 or part thereof can also be formed by or in the housing part 18.

Preferably, the transportation lock 29 is formed by multiple or only two different parts, here the gripping arm(s) 35 and a control member 39 as explained later.

The transportation lock 29, in particular, the gripping arms 35, are holding the container 3 in the delivery state (closed transportation lock 29) preferably such that the container base 21 or vent opening 34 are axially spaced from the piercing element 22, as shown in FIG. 3.

To open the transportation lock 29, the gripping arms 35 may be flexed radially outwardly. Preferably, the opening of the transportation lock 29 or the flexing of the gripping arms 35 occurs automatically when closing the nebulizer 1 or its housing completely, i.e. when snapping or pushing on the housing part 18 completely towards the upper housing part 16. During this (axial or telescopic) closing movement, the transportation lock 29 is opened and the container 3 released in axial direction preferably only in a last part of the movement and/or just little before the final completely closed position is reached or just when the final completely closed position is reached.

The closing movement of the nebulizer 1 opens the transportation lock 29 preferably automatically. In particular, the transportation lock 29 is opened by the direct or indirect interaction with or actuation by the housing of the nebulizer 1, the inner part 17 or its lower part 17*b*, a holding ring 38 bearing the spring 7 or the like. Preferably, the container 3 and/or first closure 25 are opened as well as the transportation lock 29 by means of a common actuation, here the closing movement of the nebulizer 1 or its housing or bottom part 18.

In the preferred embodiment, the transportation lock 29 comprises a control member 39, in particular a ring or the like, for actuating or opening or engaging with or pivoting preferably all gripping arms 35 simultaneously. In particular, the control member 39 or transportation lock 29 may convert a linear or axial movement into a pivot or radial movement of the gripping arms 35.

The control member 39 is shown in an upper position in FIG. 3 when the transportation lock 29 is closed. In this position, the control member 39 may secure the gripping arms 35 in the closed positions, in particular in a form-fit manner, e.g. by radially outwardly abutting portions (not shown) of the control member 39 or the like.

The control member 39 is axially moveable or shiftable in order to open the transportation lock 29. In particular, the control member 39 may be moved downwardly when completely closing the nebulizer 1 or its housing or completely pushing or snapping on the housing part 18. Preferably, the inner part 17 or ring 38 pushes the control member 39 downwardly or relatively to the gripping arms 35 so that the gripping arms 35 are released and, in particular, actively or positively opened or pivoted or flexed to open the transportation lock 29 and/or to release the container 3. In the shown embodiment, the control member 39 interacts with its axial end or an axial color or annular ring portion 40 with actuating portions 41 of the gripping arms 35 such that axially downward movement of the actuating portions 41 results in pivotation of the gripping arms 35 and radially outward flexing of the gripping arms 35. The flex characteristics of the gripping arms 35 depend on the used material, on the connection with member 37 and the like.

The control member 39 preferably opens the transportation lock 29 or gripping arms 35 positively.

FIGS. 4 and 5 show the transportation lock 29 and the gripping arms 35 in the open position, i.e. wherein the container 3 is free to move axially. In particular, control member 39 is shown in its downward end position. In this position, the control member 39 is preferably locked or secured within the bottom part 18, in particular by force-fit or form-fit or by a snap-connection, so that the transportation lock 29 and the gripping arms 35 are held open permanently- However, other constructional solutions of the transportation lock 29 are possible. In this regard, reference is made in particular to WO 2006/125577 A2 which shows some other constructional solutions, which can be realized as well.

Preferably, in the non-activated state, i.e. when the housing part 18 has not been pushed on fully, the nebulizer 1 may be locked to prevent tensioning of the pressure generator 5, i.e. in particular to prevent rotation of the inner part 17 relative to the upper housing part 16. This may be important when the nebulizer 1 is supplied in the delivery state with the pressure generator 5 not under tension. Accordingly, the inhaler 1 may have a barrier, so that the inner part 17 can only be rotated relative to the upper housing part 16 when the housing part 18 has been pushed fully on.

Alternatively or additionally, the securing member 30 may block not only pushing on of the bottom part 18 in the delivery state, but also any rotation of the inner part 17 until the securing member 30 has been opened, released or removed.

FIGS. 3 to 5 show the nebulizer 1 with a mouthpiece cover 42 covering the mouthpiece 13.

Generally, it should be pointed out that in the proposed nebulizer 1 the container 3 can preferably be inserted, i.e. incorporated in the nebulizer 1. Consequently, the container 3 is preferably a separate component. However, the container 3 may theoretically be formed directly by the nebulizer 1 or part of the nebulizer 1 or may otherwise be integrated in the nebulizer 1.

In the shown embodiment, the latching means 43 comprises multiple, here two latching lugs 31 engaging into associated latching recesses 32.

The latching arms 33 and/or latching lugs 31 are preferably formed at or by the inner part 17, in particular the lower part 17*b*. The latching recesses 32 are preferably formed at or by the housing part 18 which can be closed to cover the inserted container 3. However, the construction could also be vice versa or realized in any other suitable manner.

In the shown embodiment, the latching means 43 or housing part 18 comprises a first undercut or shoulder 44 associated to the respective latching recess 32 so that the engaging or abutting latching lug 31 holds the housing part 18 in a non-detachable or inseparable manner in the delivery state as shown in FIG. 3. This forms a first form-fit engagement or holding.

The latching means 43 forms or enables preferably a second form-fit engagement or holding of the housing part 18 in the activated state. This is realized in the shown embodiment in that the latching lugs 31 engage into further latching recesses 45 and/or behind second undercuts or shoulders 46 as shown in FIGS. 4 and 5. The second engagement of the latching means 43 is achieved preferably by completely closing the housing or housing part 18 of the nebulizer 1.

It has to be noted that the latching means 43 can be realized e.g. with only one latching lug 31, protrusion, nose, locking element or the like if desired. In this case, the above description applies preferably as well or in a similar manner.

According to a preferred aspect, the housing part 18 may be pre-mounted to the nebulizer 1, its housing or to the inner part 17 without container 3 so that the nebulizer 1, its housing or the housing part 18 can be opened again, i.e. so that the latching means 43 does not prevent opening, for later inserting or pre-installing the container 3, in particular at another factory or at a pharmacy or the like. This pre-mounting of the housing part 18 is preferably achieved in that the housing part 18 is mounted in another position, preferably another ro-tational position, on the nebulizer 1, in particular the inner part 17 of lower part 17*b*.

FIG. 6 shows in a schematic sectional view the nebulizer 1 with the pre-mounted housing part 18. Due to the other (rotational) position of the housing part 18 relative to the inner part 17, each latching lug 31 engages into a different or additional recess, groove 47 or the like. In the shown embodiment, the grooves 47 are formed in the housing part 18. The grooves 47 are axially open so that the associated latching lugs 31 may be axially drawn out of the grooves 47. Thus, the latching means 43 do not provide any latching or form-fit holding or the like in the pre-mounted state of the housing part 18. Nevertheless, the preferably radially flexible and/or biased latching lugs 31 or the latching means 43 may hold the housing part 18 by friction or force-fit so that unintentionally losing of the housing part 18 can be prevented.

Figure 7:
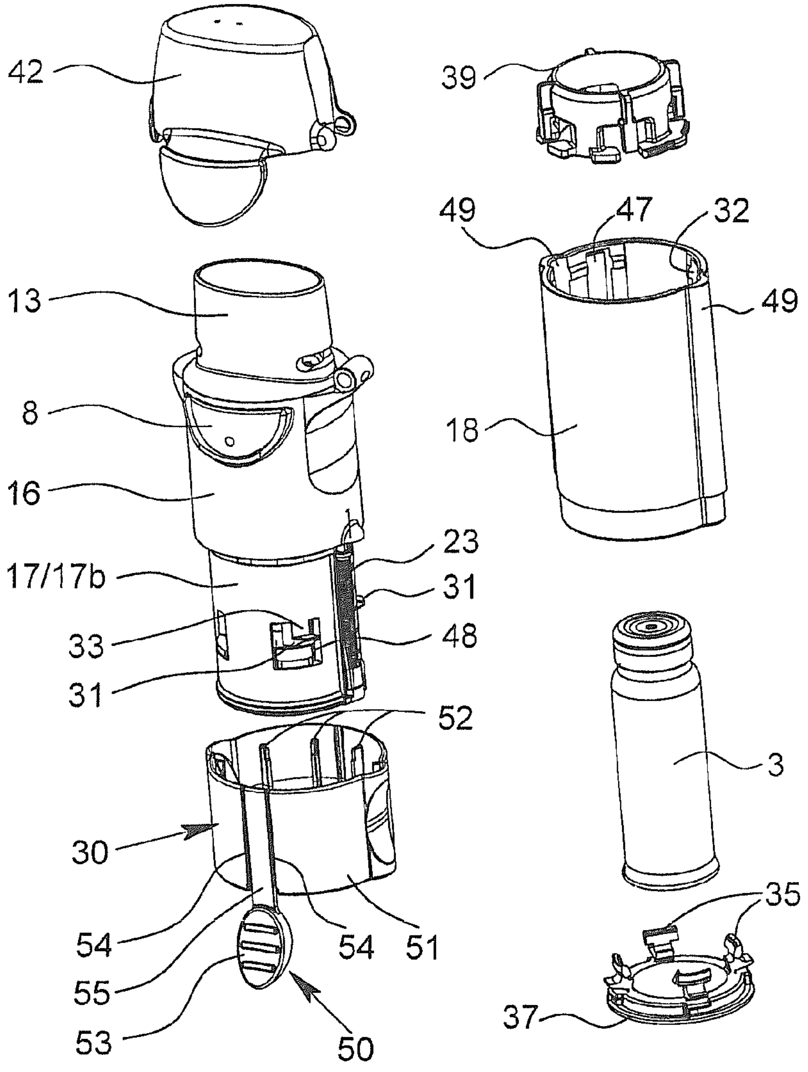
FIG. 7 a schematic explosion-like view of parts of the nebulizer including a securing member.

FIG. 7 shows the nebulizer 1 in a schematic, explosion-like view. The following parts are separated in this view: the mouthpiece cover 42, the housing comprising upper housing part 16 and inner part 17, the securing member 30, the control member 39, the housing part 18, the container 3, and the base member 37 of the housing part 18.

FIG. 7 shows that the at least one latching lug 31 and its associated latching arm 33 may be formed for example in a through hole 48 of the inner part 17/lower part 17*b*. This through hole 48, in particular multiple through holes 48, may be used for engagement of holding portions of the ring 38.

The housing part 18 and the housing or inner part 17/17*b* of the nebulizer 1 are adapted to each other such that the housing part 18 can be pushed onto the part 17/17*b* in two different rotational positions, in the present embodiment in two positions offset by 180°. For this purpose, the housing part 18 may have at least one indention 48 or any other deformation or non-circular inner cross-section, in the shown embodiment it has two indentions 49 on opposite sites, corresponding or cooperating with a respective complementary form, in the shown embodiment with the monitoring device 23 of the inner part 17/lower part 17*b*. However, other constructional solutions are possible.

The at least one latching lug 31 on one hand and the at least one latching recess 32 and the at least one groove 47 on the other hand are distributed over the circumference such that the at least one latching lug 31 engages only into the respective groove 47 in the pre-mounted state of the housing part 18 and into the respective latching recess 32/45 in the other/rotational state (delivery state or activate state), i.e. in the usual mounting position, of the housing part 18. Preferably, the two latching lugs 31 are not positioned directly opposite to each other on the circumference of part 17/17*b*, but offset. Accordingly, the schematic sections according to FIGS. 3 to 6 are not in one flat plane, but along a plane folded along the longitudinal or rotational axis or the conveying tube 9.

For assembly and pre-installing the container 3, the securing member 30 is mounted onto inner part 17/lower part 17*b* and, the housing part 18 including the pre-installed container 3 (the container 3 is held within the housing part 18 by the closed transportation lock 29) is pushed onto inner part 17/lower part 17*b*, in particular until the securing member 30 is reached and/or the first engagement of the latching means 43 is reached. Thus, the housing part 18 is connected to the nebulizer 1 or its housing or to the inner part 17 or housing part 16 in a non-detachable manner. With other words, the nebulizer 1 can not be opened any more, the container 3 can not be removed or replaced any more.

The securing member 30 can be manually opened, removed, released or destroyed to allow complete closing of the housing or nebulizer 1, i.e. to push the housing part 18 completely on the inner part 17, to reach the activated state, i.e. to allow fluidic connection or opening of the container 3.

Preferably, the securing member 30 comprises an actuator 50 to open, remove, release or destroy the securing member 30. The actuator 50 is preferably non-detachable from the securing member 30. Preferably, the securing member 30 is made as one piece, in particular integrally with the actuator 50.

Preferably, the securing member 30 is made of plastics. However, the securing member 30 can be made of any other suitable material or from different materials. In particular, the securing member 30 is molded.

The securing member 30 comprises preferably a body 51. The securing member 30 or body 51 is preferably hollow and/or preferably forms a sleeve, ring, loop, banderole, or the like. In particular, it forms a closed sleeve or ring.

In the shown embodiment, the actuator 50 may form part of the circumferential wall, ring or sleeve formed by the body 51.

The actuator 50 is preferably inseparable from the securing member 30 or body 51 even if the securing member 30 is opened, removed, released or destroyed to allow fluidic connection opening of the container 3 and/or to allow entering of the activated state.

The securing member 30 or body 51 preferably comprises engagement means, such as at least one stop 52, protruding radially inwardly and/or engaging between the housing part 18 on one hand and the nebulizer 1, its housing, the upper housing part 16 or the ring 38 on the other hand, in particular to form an axial stop or abutment for the housing part 18 in the delivery state against movement into the activated state. In the present embodiment, the engagement means are preferably formed by ribs or protrusions extending in particular axially and protruding radially inwardly. Preferably, the engagement means are and/or covered and/or formed by the body 51. However, other constructional solutions are possible as well.

In the following, the term "to open the securing member" or similar formulations shall include that the securing member 30 is removed, release, destroyed or the like.

To open the securing member 30, a user (not shown) pulls, tears, pivots, tilts, pushes, presses and/or removes the actuator 50. For this purpose, the actuator 50 may form or may be formed by a handhold 53, grip, lever, tag, flap, ring, clip or the like as shown in some examples in the further figures.

The securing member 30 or body 51 comprises preferably at least one predetermined breaking line 54 in order to facilitate opening and/or to ensure a defined opening. For example, the breaking line 54 may extend along and/or adjacent to the actuator 50 and/or on both or opposite sides of the actuator 50.

The breaking line 54 can be defined or pre-formed in particular by respective thinning of the material, a respective perforation or the like, in particular of the body 51.

In the shown embodiment, the breaking line 54 extends at least essentially in axial direction (the term "axial direction" means generally at least essentially parallel to the longitudinal or central axis or rotational axis of the nebulizer 1 and/or to the main dispensing direction of the aerosol 14/nebulizer 1).

Preferably, the securing member 30 locks the housing part 18 against rotation. This can be achieved in that the securing member 30 engages with the nebulizer 1 or upper housing part 16 and with the lower housing part 18 respectively in a form-fit manner, e.g. by axial engagement and/or by at least partially covering the preferably non-circular outer contour of the respective parts 16/18. However, other constructional solutions are possible as well.

After pulling the actuator 50, the securing member 30 or body 51 is open, preferably along at least one breaking line 54, so that the closed ring, sleeve or banderole of the securing member 30/body 51 is open and can be detached from the nebulizer 1 in particular by respective moving or flexing the free ends of the body 51 away from each other. Thus, the securing member 30 can be detached from the nebulizer 1. This allows to push the housing part 18 onto the inner part 17, i.e. towards the upper housing part 16, so that the container 3 is fluidically opened or connected and the housing of the nebulizer 1 is completely closed.

It has to be noted that the securing means 30 or the body 51 is preferably sufficiently flexible such when the actuator 50 has been pulled and the securing means 30 has been opened, the body 51 can be detached from the nebulizer 1.

In the present embodiment, the actuator 50 is directed to or points towards the housing part 18 and/or away from the mouthpiece 13 and/or essentially in axial direction.

In the following, further embodiments of the securing member 30 are explained with reference to the further figures, wherein only major differences are discussed or emphasized. The previous explanations and description of the previous embodiment and of the further embodiments apply preferably in addition or in a similar manner, even if not repeated.

Figure 8A:
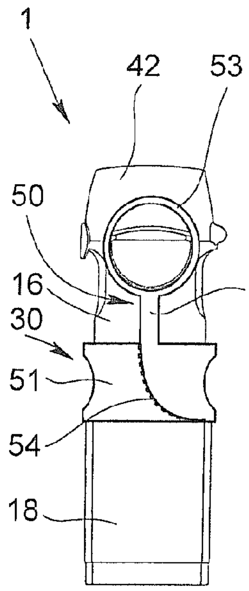
FIG. 8 A a side view of the nebulizer with another securing member.
FIG. 8B a side view of the nebulizer perpendicular to the view of FIG. 8 A.
Figure 8B:
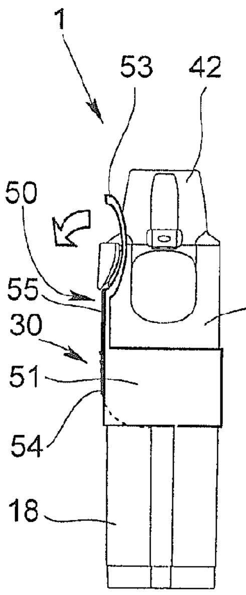

FIG. 8A shows a side view (front face) of the nebulizer 1 with another securing member 30 and FIG. 8B shows it in a view of a transversal side (side face). In this embodiment, the actuator 50 extends upwards so that the handhold 53 extends at least in front of the mouthpiece cover 42 covering the releasing element 8. Preferably, the actuator 50 or its handhold 53 engages with the mouthpiece cover 42 or covers the mouthpiece cover 42 partially or engages therewith such that the actuator 50/handhold 53 has to be pulled (as schematically indicated in FIG. 8*b* by an arrow) before the mouthpiece cover 42 can be opened. This facilitates an intuitive handling of the nebulizer 1.

The actuator 50 extends essentially in axial direction and/or towards the dispensing and/or mouthpiece 13 of the nebulizer 1.

The securing means 30 comprises in this embodiment preferably only one breaking line 54.

The breaking line 54 is essentially continuously curved and, for example, at least from an essentially axial extension at the upper circumference of the body 51 to an at least essentially circumferential direction at the lower circumference of the body 51.

The actuator 50 comprises preferably a portion 55 connecting the handhold 53, grip, lever, tag, flap, ring, clip or the like with the body 51. This portion 55 is preferably stem-like and/or flexible.

Figure 9A:
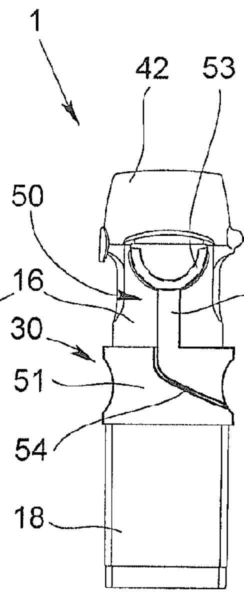
FIG. 9A a side view of the nebulizer with another securing member.
Figure 9B:
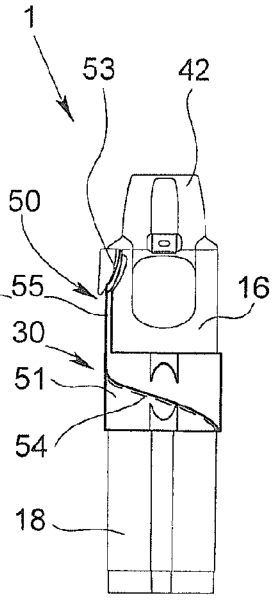
FIG. 9B a side view of the nebulizer perpendicular to the view of FIG. 9A.

FIG. 9A shows a side view (front face) of the nebulizer 1 with another securing member 30 and FIG. 9B shows it in a view of a transversal side (side face). This embodiment differs from the embodiment according to FIG. 8 essentially in that the actuator 50 or its handhold 53 extends below the part of the mouth-piece cover 42 which covers the releasing element 8. Thus, the mouthpiece cover 42 has to be opened first before the actuator 50 or its handhold 53 can be actuated, in particular grabbed or pulled. This allows also an intuitive handling. Namely, the actuator 50 or its handhold 53 is located at least partially above or on the releasing element 8 so that the user will usually actuate the actuator 50 before pressing the releasing element 8.

In this embodiment, the breaking line 54 extends more or less helically around the body 51.

Figure 10A:
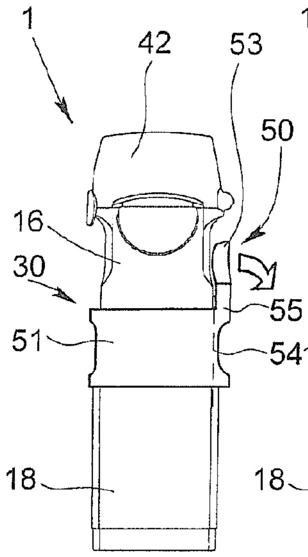
FIG. 10A a side view of the nebulizer with another securing member.
Figure 10B:
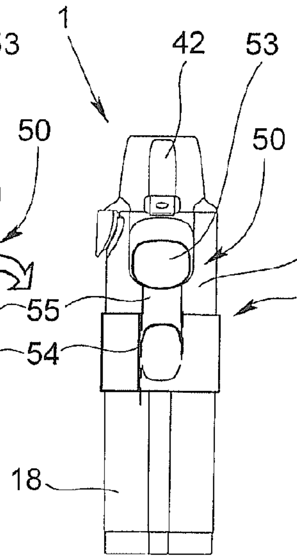
FIG. 10B a side view of the nebulizer perpendicular to the view of FIG. 10A.

FIG. 10A shows a side view (front face) of the nebulizer 1 with another securing member 30 and FIG. 10B shows it in a view of a transversal side (side face). In this embodiment, the actuator 50 is located on another side than the releasing element 8 (which is not visible because it is covered by the mouthpiece cover 42). In particular, the actuator 50 or its handhold 53 is located on a transversal side or side face relative to the side (front face) with the operating button, i.e. releasing element 8, of the nebulizer 1.

In this embodiment, the breaking line 54 runs at least essentially in axial direction.

Figure 11A:
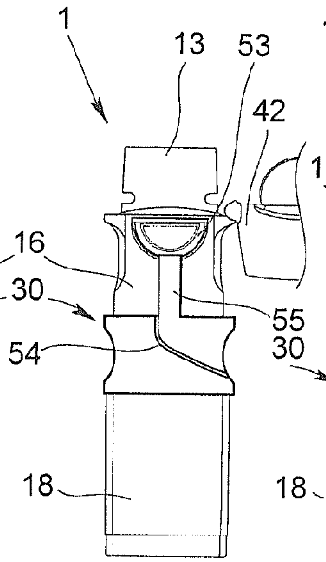
FIG. 11A a side view of the nebulizer with another securing member.
Figure 11B:
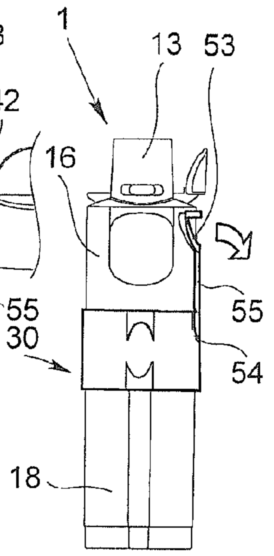
FIG. 11B a side view of the nebulizer perpendicular to the view of FIG. 11 A.

FIG. 11A shows a side view (front face) of the nebulizer 1 with another securing member 30 and FIG. 11B shows it in a view of a transversal side (side face). This embodiment is very similar to the embodiment according to FIG. 9. Here, the nebulizer 1 is shown with open mouthpiece cover 42. Further, the handhold 53 is formed slightly differently. A half-circular form is closed by a substantial horizontal connection. In the embodiment according FIG. 9, the handhold 53 has an essentially half-circular or U-form, but does not form a closed loop or ring-like structure as shown in the embodiments according to FIGS. 8 and 11.

Figure 12A:
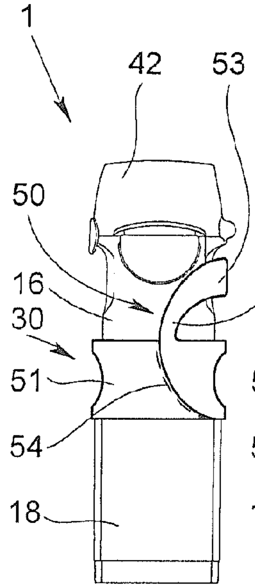
FIG. 12A a side view of the nebulizer with another securing member.
Figure 12B:
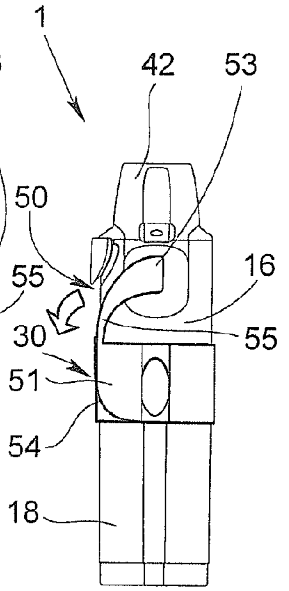
FIG. 12B a side view of the nebulizer perpendicular to the view of FIG. 12A.

FIG. 12A shows a side view (front face) of the nebulizer 1 with another securing member 30 and FIG. 12B shows it in a view of a transversal side (side face). In this embodiment, the actuator 50 is located at a side face of the nebulizer 1, similar to the embodiment according to FIG. 10. Further, the actuator 50 or its portion 55 is curved and extends more or less from the front face with the releasing element 8 (shown in FIG. 12A) to the side face (shown in FIG. 12B).

In this embodiment, the actuator 50 is at essentially strip-like and/or broadens towards its free end.

Further, the actuator 50 continues essentially the curvature of the breaking line 54. The actuator 50 or its portion 55 and the breaking line 54 extend essentially along a half circle.

The opening of the securing member 30 or actuator 50 is schematically indicated by the arrow shown in FIG. 12B.

Figure 13A:
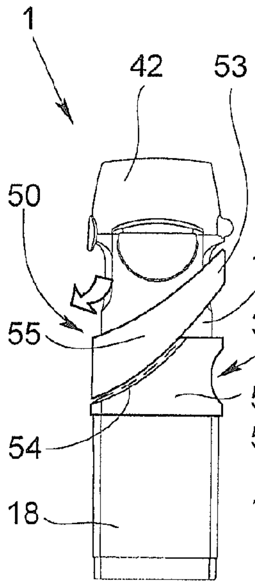
FIG. 13 A a side view of the nebulizer with another securing member.
FIG. 13B a side view of the nebulizer perpendicular to the view of FIG. 13 A.
Figure 13B:
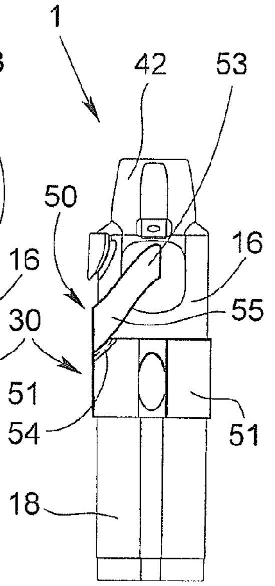

FIG. 13A shows a side view (front face) of the nebulizer 1 with another securing member 30 and FIG. 13B shows it in a view of a transversal side (side face). This embodiment is similar to the embodiment according to FIG. 12. In the present embodiment, the actuator 50 is differently curved and is at least essentially tapered or narrowed to its free end. Here, the actuator 50 or its portion and the breaking line 54 form a soft curve or part of a helical line.

Figure 14A:
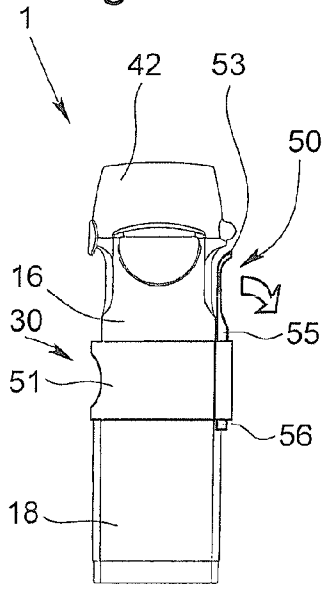
FIG. 14A a side view of the nebulizer with another securing member.
Figure 14B:
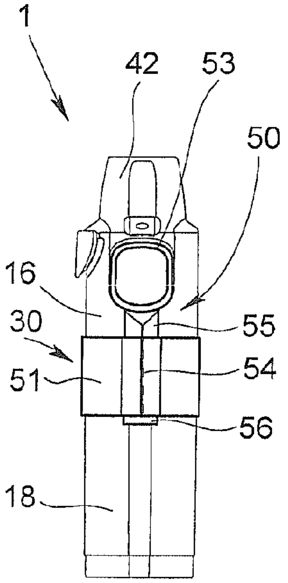
FIG. 14B a side view of the nebulizer perpendicular to the view of FIG. 14A.
Figure 14C:
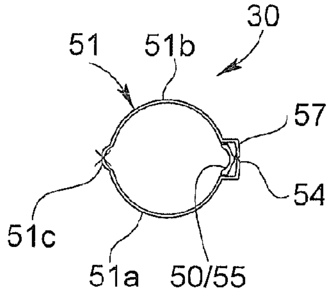
FIG. 14C a schematic horizontal section of the securing member of the nebulizer according to FIG. 14A.

FIG. 14A shows a side view (front face) of the nebulizer 1 with another securing member 30 and FIG. 14B shows it in a view of a transversal side (side face). FIG. 14C shows a horizontal section of the securing member 30 without the nebulizer 1. In this embodiment, the actuator 50 is connected via a living hinge 56 (shown in FIGS. 14A and 14B at the lower end of the body 51) and is tilted upwards so that it passes or extends within the body 51 and extends towards the mouthpiece 13 and/or in axial direction. The actuator 50 is located at the side face of the nebulizer 1. To open the securing member 30, the actuator 50 is tilted or pivoted radially outwardly around the living hinge 56 wherein the portion 55 opens the body 51. For this purpose, the actuator 50 or portion 55 preferably forms a rib or cutting edge 57 as schematically shown in the section according to FIG. 14B.

The body 51 is formed preferably in one piece. The body 51 can comprise or form two parts or halves 51*a* and 51*b* which can be connected via a pivotal joint or hinge 51*c*, such as a living hinge. In this case, the parts or halves 51*a* and 51*b* may be relatively stiff or rigid. To open the body 51, the two parts or halves 51*a* and 51*b* are pivoted away from each other around the hinge 51*c*. This is possible after actuating the actuator 50, in particular after opening or breaking the body 51 along the breaking line 54.

It has to be noted that the concept of two parts or halves 51*a* and 51*b* connected by a pivotal connection or hinge 51*c* can be used in any other embodiment as well. Further, the two parts or halves 51*a* and 51*b* may be formed as separate parts and connected via any other type of joint or hinge 51*c*.

It has to be noted that the body 51 forms or comprises preferably an at least essentially closed and/or smooth surface over the circumference. However, other designs and constructions are possible as well.

Figure 15A:
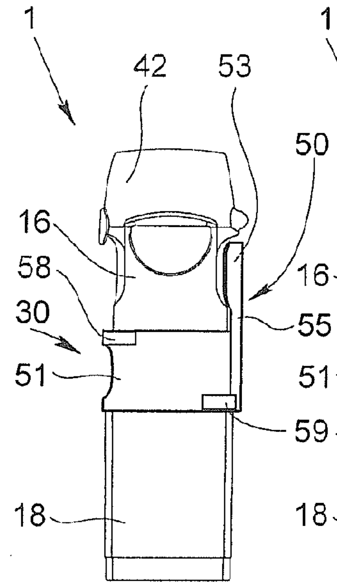
FIG. 15 A a side view of the nebulizer with another securing member.
FIG. 15B a side view of the nebulizer perpendicular to the view of FIG. 15 A.
Figure 15B:
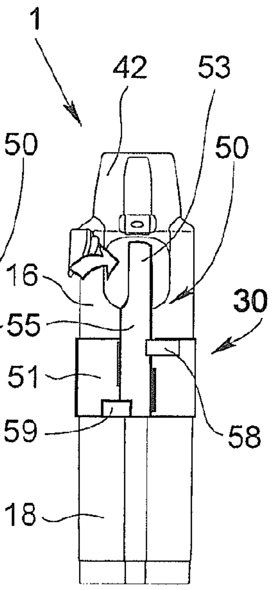

FIG. 15 A shows a side view (front face) of the nebulizer 1 with another securing member 30 and FIG. 15B shows it in a view of a transversal side (side face). Here, the actuator 50 has to be actuated more or less in a tangential direction perpendicular to the axial direction. In the previous embodiments, the actuator 50 has to be actuated at least essentially radially outwardly, in particular by radial pulling, which can be combined with a downward movement or downward pivotation and/or with a circumferential movement.

In the present embodiment, the actuator 50 acts as a lever which is supported on one circumferential side in the upper region of the body 51 by a first connection or bearing 58 and on the other circumferential side in a lower region of the body 51 by a second connection or bearing 59. The connections or bearings 58, 59 are axially offset. When the actuator 50 is operated or tilted, the adjacent parts of the body 51 are moved away from each other. Thus, the diameter of the body 51 is increased and the securing member 30 can be disengaged and moved over the housing part 18 in order to detach the securing member 30 from the nebulizer 1.

Figure 16A:
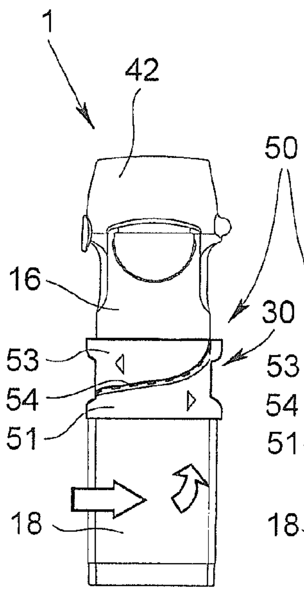
FIG. 16A a side view of the nebulizer with another securing member.
Figure 16B:
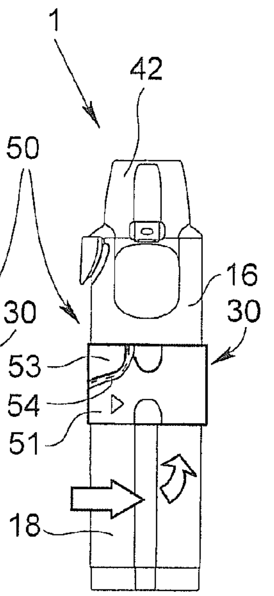
FIG. 16B a side view of the nebulizer perpendicular to the view of FIG. 16A.

FIG. 16A shows a side view (front face) of the nebulizer 1 with another securing member 30 and FIG. 16B shows it in a view of a transversal side (side face). In this embodiment, the actuator 50 is formed by the body 51 or part of the body 51. In particular, the actuator 50 does not comprise a handhold 53 or the like and/or a portion 55 extending or protruding from the body 51. The handhold 53 is preferably formed by a portion of the body 51 forming a flap or end-part, preferably adjacent to the breaking line 54. This end portion can be grabbed manually to open the securing member 30 or its body 51. Alternatively and preferably the securing member 30 or its body 51 is opened—in particularly along the breaking line 54—by turning the housing part 18 relative to the nebulizer 1/upper housing part 16. In this case, the securing member 30 or its body 51 is opened by torsioning. In order to allow turning of the housing part 18, it may be necessary to allow that inner part 17 can be turned relative to the nebulizer 1 or upper housing part 16. However, the nebulizer 1 could be respectively adapted also in a different manner. The turning of the housing part 18 to open the securing member 30 or body 51 is schematically indicated in FIG. 16 by arrows.

The breaking line 54 extends preferably at least essentially along a helical line of the body 51. However, the breaking line 54 can follow other courses or paths.

Figure 17A:
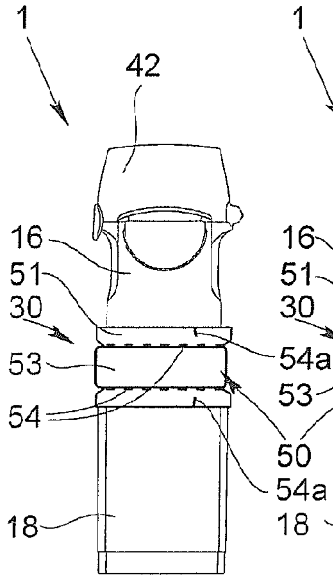
FIG. 17A a side view of the nebulizer with another securing member.
Figure 17B:
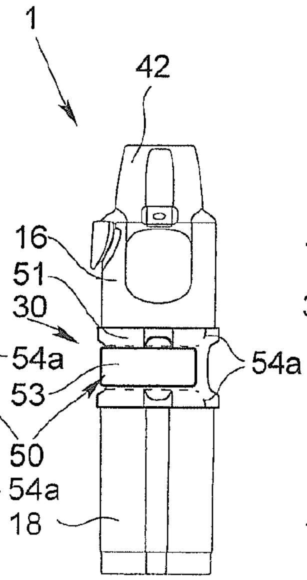
FIG. 17B a side view of the nebulizer perpendicular to the view of FIG. 17A.

FIG. 17A shows a side view (front face) of the nebulizer 1 with another securing member 30 and FIG. 17B shows it in a view of a transversal side (side face). In this embodiment, the actuator 50 is formed by or integrated into the body 51 similar as in the embodiment according to FIG. 16. In particular, the actuator 50 does not comprise a handhold 53 and/or portion 55 extending or protruding from the body 51, in particular in axial direction. In the present embodiment, the actuator 50 extends at least essentially in circumferential direction and/or around or along the body 51. Preferably, the actuator 50 or its handhold 53 forms, comprises or is formed by a flap, a hanger, a clip, a strap or an ear as schematically shown in FIG. 17.

In the present embodiment, the actuator 50 or its handhold 53 is pulled at least essentially in circumferential or tangential direction and/or around the body 51 to open the securing member 30.

The securing member 30 comprises one or two breaking lines 54 extending at least essentially along a circumference of the body 51 with axially curved or ends or start portions 54A.

Figure 18A:
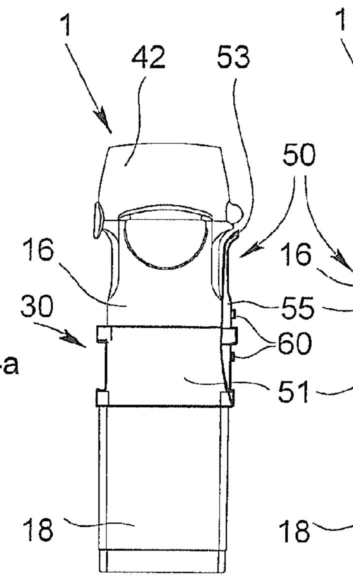
FIG. 18A a side view of the nebulizer with another securing member.
Figure 18B:
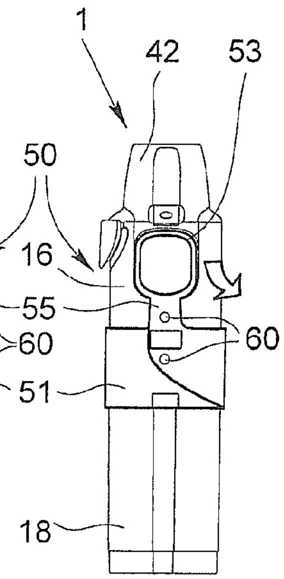
FIG. 18B a side view of the nebulizer perpendicular to the view of FIG. 18A.

FIG. 18 A shows a side view (front face) of the nebulizer 1 with another securing member 30 and FIG. 18B shows it in a view of a transversal side (side face). In this embodiment, the securing member 30 or body 51 does not comprise or form an initially closed loop, banderole, ring or sleeve (between the housing parts 16 and 18) as in the previous embodiments. Instead, the body 51 is closed by means of connecting means 60, such as a rivet or pin connection as indicated in FIG. 18. In particular, the connecting means 60 connects overlapping part or ends of the body 51 and/or provides a releasable connection to allow opening of the body 51 and detachment of the securing member 30.

The actuator 50 is located at the side face of the nebulizer 1. The handhold 53 is ring-like preferably similar to the one shown in the embodiment according to FIG. 14. To open the securing member 30 or body 51, the actuator 50 or its handhold 53 has to be pulled radially outwards, downwards and/or sidewards as schematically indicated by an arrow in FIG. 18B. Thus, the connecting means 60 is opened or released.

Figure 19A:
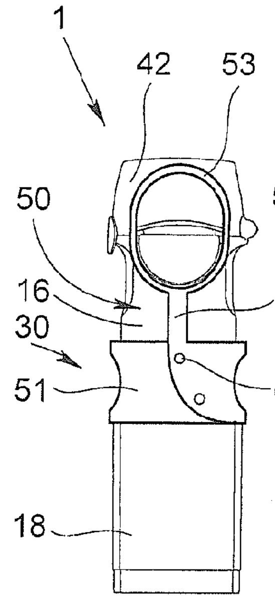
FIG. 19 A a side view of the nebulizer with another securing member.
FIG. 19B a side view of the nebulizer perpendicular to the view of FIG. 19A.
Figure 19B:
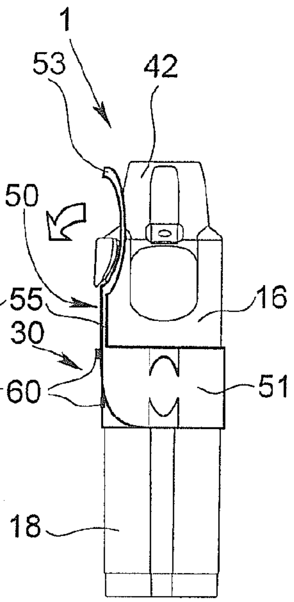

FIG. 19A shows a side view (front face) of the nebulizer 1 with another securing member 30 and FIG. 19B shows it in a view of a transversal side (side face). The securing member 30 or body 51 comprises connecting means 60 similar to the embodiment according to FIG. 18. The actuator 50 is at least essentially similar to the one shown in the embodiment according to FIG. 8. The actuator 50 is located at the front face of the nebulizer 1.

The securing member 30 or body 51 is opened in a similar manner as in case of the embodiment according to FIG. 18 and/or by moving the actuator 50 or its handhold 53 at least essentially in the direction of the arrow shown in FIG. 19B.

Figure 20A:
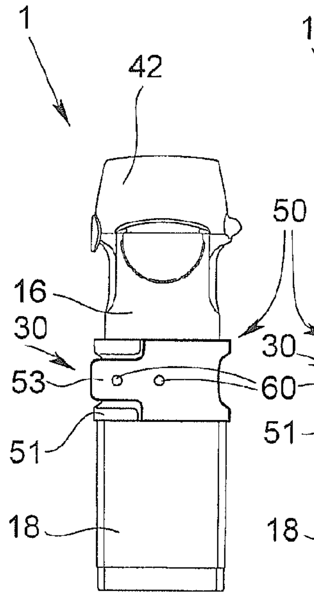
FIG. 20A a side view of the nebulizer with another securing member.
Figure 20B:
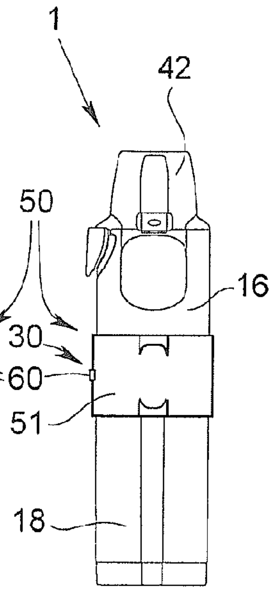
FIG. 20B a side view of the nebulizer perpendicular to the view of FIG. 20A.

FIG. 20A shows a side view (front face) of the nebulizer 1 with another securing member 30 and FIG. 20B shows it in a view of a transversal side (side face). In this embodiment, the securing member 30 or its body 51 comprises connecting means 60 as well, i.e. similar to the ones shown in the embodiments according to FIGS. 18 and 19.

In the present embodiment, the actuator 50 is basically similar to the one shown in the embodiment according to FIG. 17, i.e. it extends at least essentially in circumferential direction and/or along or on the body 51. Preferably, the actuator 50 is strap- or flap-like. The actuator 50 or its handhold 53 has to be pulled radially to open the connecting means 60 and, thus, to open the body 51/securing member 30.

Figure 21A:
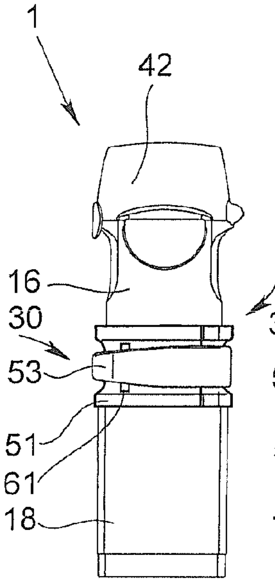
FIG. 21A a side view of the nebulizer with another securing member.
Figure 21B:
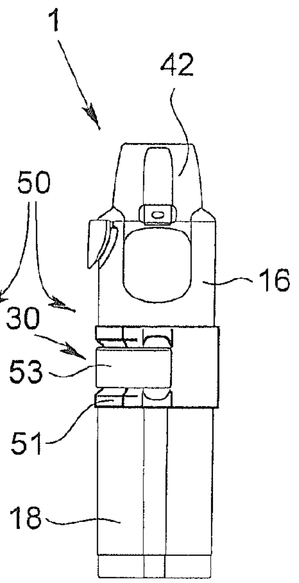
FIG. 21B a side view of the nebulizer perpendicular to the view of FIG. 21A.

FIG. 21 A shows a side view (front face) of the nebulizer 1 with another securing member 30 and FIG. 2 IB shows it in a view of a transversal side (side face). This embodiment is similar to the embodiment according to FIG. 20. However, the securing member 30 or body 51 does not comprise connecting means 60. Instead, the securing member 30, body 51 or actuator 50 is sufficiently stiff or rigid such that it secures itself in the delivery state shown in FIG. 21. To open the securing member 30 or body 51, the actuator 50 or its handhold 53 has to be pulled radially outwardly and/or tangentially and/or in circumferential direction to bend the actuator and/or the securing member 30/body 51 open so that it can be detached from the nebulizer 1. In order to facilitate grabbing of the actuator 50 or its handhold 53, the body 51 may comprise a rib or protrusion 61 to hold the actuator 50/handhold 53 in a slightly elevated position.

Figure 22A:
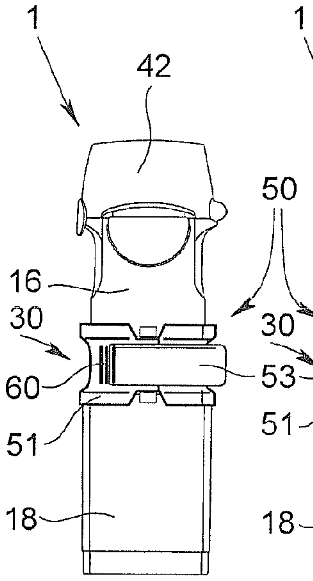
FIG. 22A a side view of the nebulizer with another securing member.
Figure 22B:
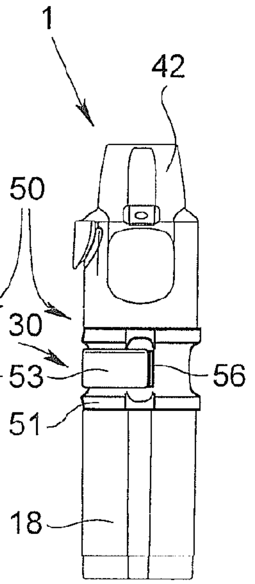
FIG. 22B a side view of the nebulizer perpendicular to the view of FIG. 22A.

FIG. 22A shows a side view (front face) of the nebulizer 1 with another securing member 30 and FIG. 22B shows it in a view of a transversal side (side face). This embodiment is very similar to the one shown in FIG. 21. In the present embodiment, the actuator 50 is connected via the living hinge 56 to the body 51 and/or connectable via connecting means 60 to the body. Preferably, the connecting means 60 can be opened again and/or allow a hook-like fixing of the actuator 50 or its handhold 53.

Figure 23A:
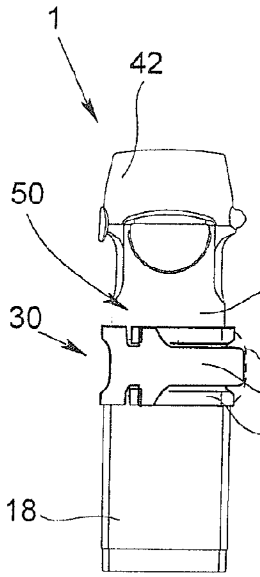
FIG. 23 A a side view of the nebulizer with another securing member.
FIG. 23B a side view of the nebulizer perpendicular to the view of FIG. 23A.
Figure 23B:
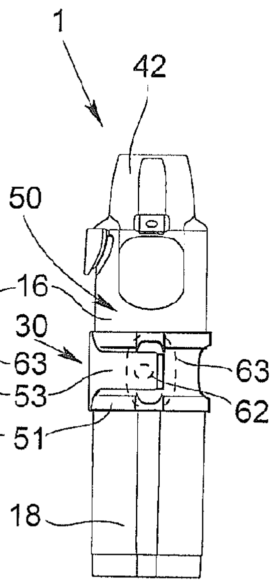

FIG. 23 A shows a side view (front face) of the nebulizer 1 with another securing member 30 and FIG. 23B shows it in a view of a transversal side (side face). This embodiment is similar to the ones shown in FIGS. 21 and 22. Here, the actuator 50 or its handhold 53 may be releasably fixed in the closed or mounted position by means of an adhesive connection, e.g. my means of a glue point 62 as indicated in FIG. 23B, or by means of a preferably self-adhesive tape 63 indicated in FIG. 23A or the like. The gluing or tape 63 can be broken or released or detached to actuate/pull the actuator 50 or its handhold 53.

Figure 24A:
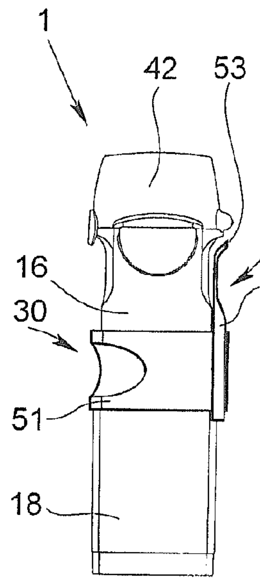
FIG. 24A a side view of the nebulizer with another securing member.
Figure 24B:
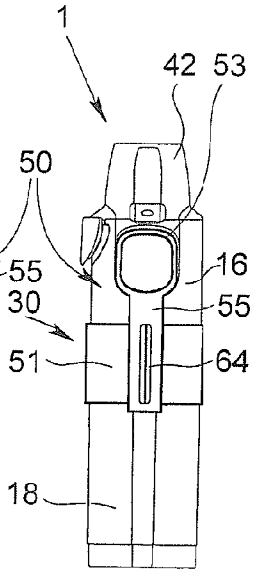
FIG. 24B a side view of the nebulizer perpendicular to the view of FIG. 24A.

FIG. 24 A shows a side view (front face) of the nebulizer 1 with another securing member 30 and FIG. 24B shows it in a view of a transversal side (side face). In the present embodiment, the securing member 30 is not a single piece, but consists of multiple or at least two parts, in particular in contrast to the previous embodiments. In the present embodiment and in the embodiments shown in FIGS. 25 and 26, the actuator 50 is not formed in one piece or integrally with the body 51, but made as a piece separate from body 51.

In the embodiment according to FIG. 24, the actuator 50 comprises a through hole or recess 64, into which the free ends of the body 51 are inserted. The free ends can be bent, folded or thickened so that the actuator 50 is held by or connected to the body 51 by force-fit or form-fit. When the actuator 50 is tilted, pivoted or pulled, in particular as indicated by the arrow shown in FIG. 24A, the actuator 50 is drawn from the free ends of the body 50 and, thus, detached from the body 51. Then, the body 51 is open and can be detached from the nebulizer 1.

In the shown embodiment, the actuator 50 is designed and/or located similar as in case of the embodiment according to FIG. 14. In particular, it extends in axial direction and/or is located on the side face. Alternatively or additionally, the body 51 may be formed by two parts or halves 51*a* and 51*b* which may be pivoted relatively to each other to open the body 51 as described in particular in connection with FIG. 14C.

Figure 25A:
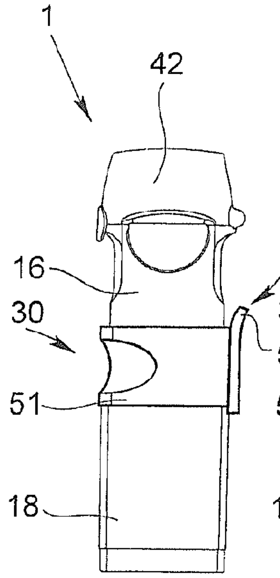
FIG. 25 A a side view of the nebulizer with another securing member.
FIG. 25B a side view of the nebulizer perpendicular to the view of FIG. 25A.
Figure 25B:
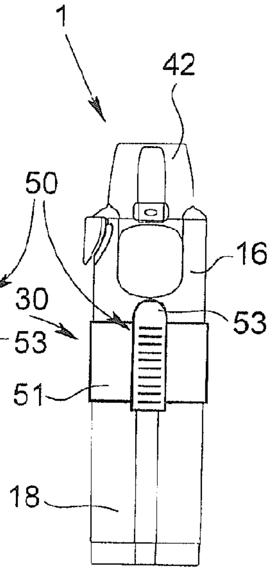

FIG. 25 A shows a side view (front face) of the nebulizer 1 with another securing member 30 and FIG. 25B shows it in a view of a transversal side (side face). This embodiment is very similar to the embodiment according to FIG. 24. However, the actuator 50 is axially clipped or radially pushed onto the free ends of the body 51 and/or holds the free ends of the body 51 together like a clamp in the embodiment according to FIG. 25. The actuator 50 can be opened or detached preferably by radial pulling and/or axial pushing.

Figure 26A:
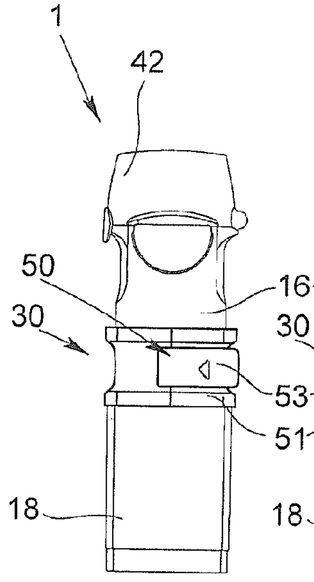
FIG. 26A a side view of the nebulizer with another securing member.
Figure 26B:
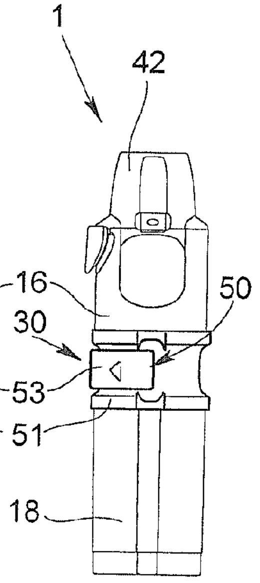
FIG. 26B a side view of the nebulizer perpendicular to the view of FIG. 26A.

FIG. 26A shows a side view (front face) of the nebulizer 1 with another securing member 30 and FIG. 26B shows it in a view of a transversal side (side face). This embodiment is very similar to the embodiment according to FIG. 25. However, the actuator 50 forms a circumferential clamp closing or holding the body 51 together. To open the securing member 30 or body 51, the actuator 50 is pulled radially outwards and/or shifted, in particular in circumferential direction or in any other suitable direction and thus released or detached.

Figure 27A:
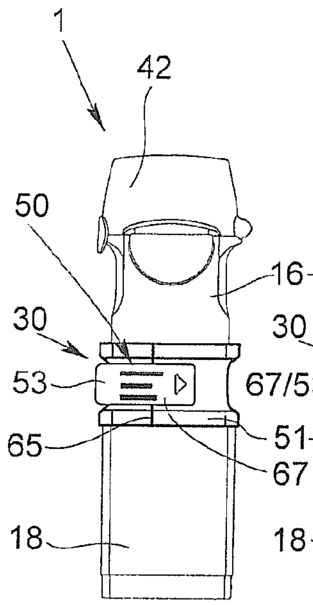
FIG. 27A a side view of the nebulizer with another securing member.
Figure 27B:
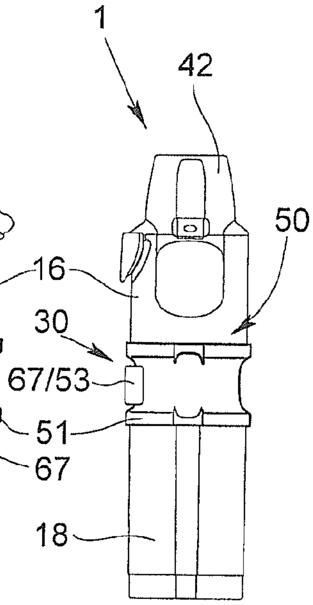
FIG. 27B a side view of the nebulizer perpendicular to the view of FIG. 27A.

FIG. 27A shows a side view (front face) of the nebulizer 1 with another securing member 30 and FIG. 27B shows it in a view of a transversal side (side face). This embodiment, the actuator 50 is made from a different material than the body 51 in contrast to the previous embodiments. Preferably, the actuator 50 is formed by a preferably self-adhesive tap 66, tag, label or tape and/or made of any other suitable, preferably flexible or foil-like material. The actuator 50 extends preferably in circumferential direction and closes the body 50, in particular by adhering the actuator 50 over a radial gap or slit 65 of the body 50. To open the securing member 30 or body 51, the actuator 50 is broken, torn or drawn from the body 51. Then, the body 51 can be detached from the nebulizer 1.

Figure 28A:
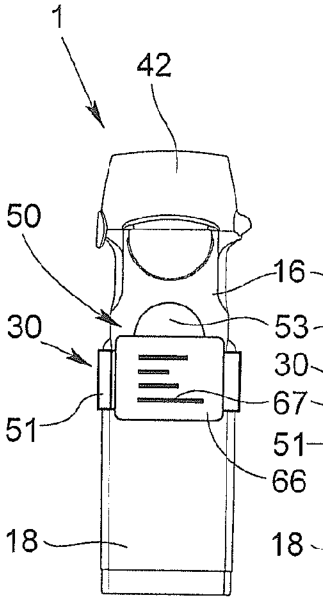
FIG. 28 A a side view of the nebulizer with another securing member.
FIG. 28B a side view of the nebulizer perpendicular to the view of FIG. 28A.
Figure 28B:
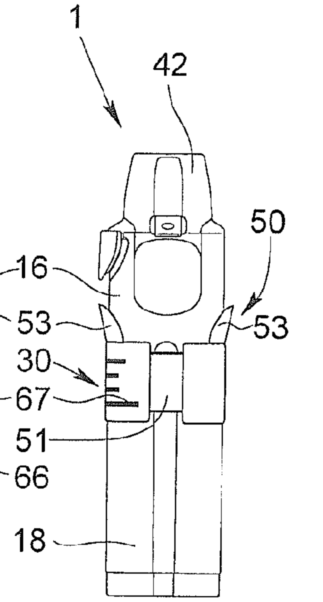

FIG. 28A shows a side view (front face) of the nebulizer 1 with another securing member 30 and FIG. 28B shows it in a view of a transversal side (side face). This embodiment is very similar to the embodiment according to FIG. 27. In this embodiment, the actuator 50 is larger, in particular in axial direction, than the body 51 and/or the actuator 50 of FIG. 27. Further, the securing member 30, body 51 or the actuator 50 may comprise or support or form a tap 66 which may be self-adhesive or adhered to any part thereof and/or which may at least partly cover any part thereof, such as the actuator 50 or its portion 55.

It has to be noted in general that the securing member 30 or actuator 50 or its portion 55 can be provided with symbols 67, in particular such as numerals, letters, colors, codes, signs and/or instructions or the like, in particular relating to the handling or opening and/or relating to the nebulizer 1, its medicament or fluid 2 or the like. This can be realized by using a respective, preferably self-adhering plate, tag 66 or tap or the like which could be used in addition to the actuator 50 or form the actuator 50 or any other part of the securing member 30. Alternatively or additionally, such symbols, signs, instructions or the like can be formed by molding, printing or the like, in particular on any suitable surface of any component of the securing member 30.

As already mentioned, individual features, aspects and/or principles of the embodiments described may also be combined with one another as desired and may be used particularly in the known nebulizer 1 according to FIGS. 1 and 2 but also in similar or different nebulizers.

Unlike freestanding equipment or the like the proposed nebulizer 1 is preferably designed to be portable and in particular is a mobile hand operated device.

The proposed solution may, however, be used not only in the nebulizers 1 specifically described here but also in other nebulizers or inhalers, e.g. powder inhalers or so-called metered dose inhalers.

Preferably, the fluid 2 is a liquid, as already mentioned, especially an aqueous pharmaceutical formulation. However, it may also be some other pharmaceutical formulation, a suspension or the like.

According to an alternative embodiment the fluid 2 may also comprise particles or powder. In this case, instead of the expulsion nozzle 12, some other kind of supply device may be provided, especially an expulsion opening (not shown) or a supply channel (not shown) for supplying the fluid to or powder or the like into the mouthpiece 13. The optional air supply opening 15 then serves to supply ambient air preferably in parallel so as to general or allow an airflow with a sufficient volume for breathing in or inhaling through the mouthpiece 13.

If necessary the fluid 2 may also be atomized by means of a propellant gas.

Preferred ingredients and/or formulations of the preferably medicinal fluid 2 are listed in particular in WO 2009/047173 A2 which is incorporated herewith by reference. As already stated, these may be aqueous or non-aqueous solutions, mixtures, formulations containing ethanol or free from solvent, or the like.

In the following, a further, preferred embodiment of the inhaler or nebulizer 1 according to the present invention will be described in detail with reference to FIGS. 29 to 32 wherein only essential differences will be emphasized so that the previous remarks and explications preferably in a corresponding or similar manner. This nebulizer 1 comprises in the delivery state a pre-installed container and the securing member as already described. Although, it is not shown in the following drawings.

Figure 29:
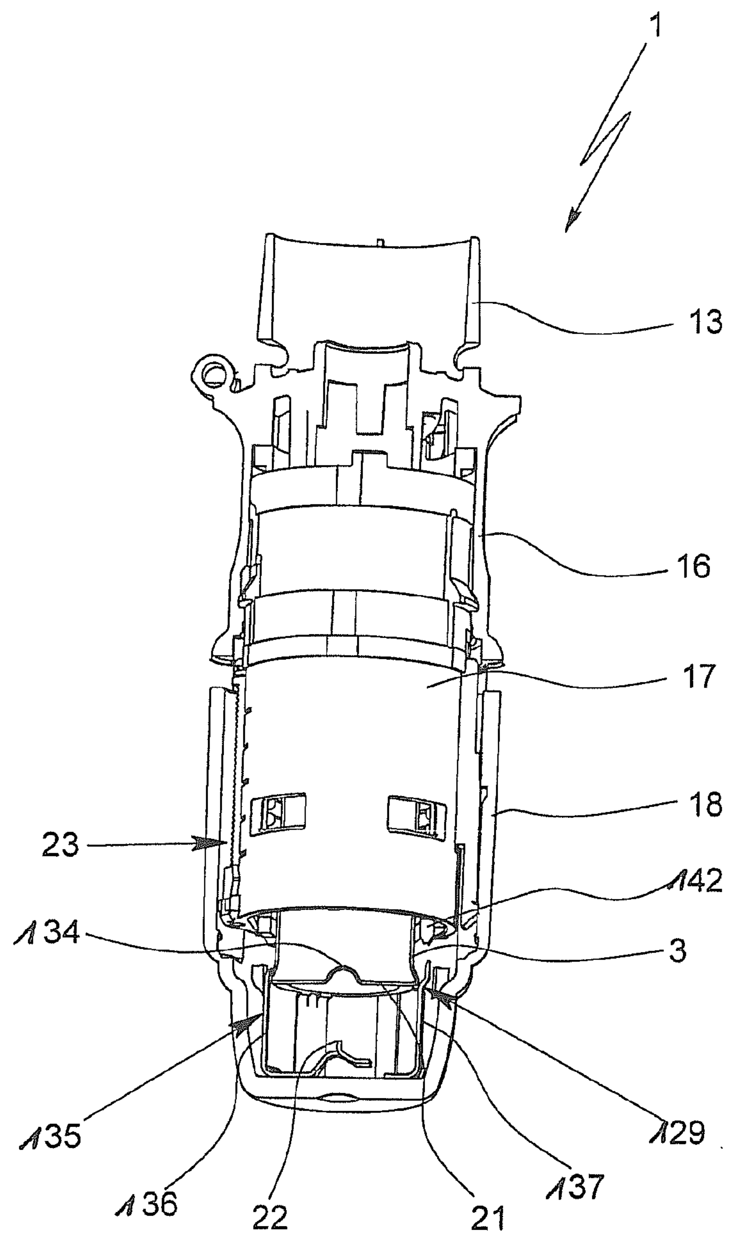
FIG. 29 a schematic section of a nebulizer with a partly closed housing and with a securing means in a housing part holding unmoveably a container in the nebulizer.

FIG. 29 shows in a very schematic, partially sectional view the nebulizer 1. The nebulizer 1 is shown a transitional state from the delivery state to the activated state with not completely closed housing or housing part 18. The housing part 18 has already been pushed on the inner part 17 more than initially provided in the delivery state such as shown in FIG. 3. Therefore, the container 3 has already been opened in the state shown in FIG. 29. Further, the securing member 30, which preferably secures the housing part 18 in the delivery state against pushing on the inner part 17, has already been released or opened or removed in the state shown in FIG. 29.

The nebulizer 1 or its housing comprises a securing means 135 for holding the container 3 such that the container 3 is moveable back and forth for the conveying of the fluid 2, pressure generation and/or nebulization, but is inseparable from the housing or housing part 18, and/or such that the container 3 is unmoveably held in the delivery state of the nebulizer 1.

The securing means 135 is located or arranged preferably at or in the housing part 18 as shown in FIG. 29.

Figure 30:
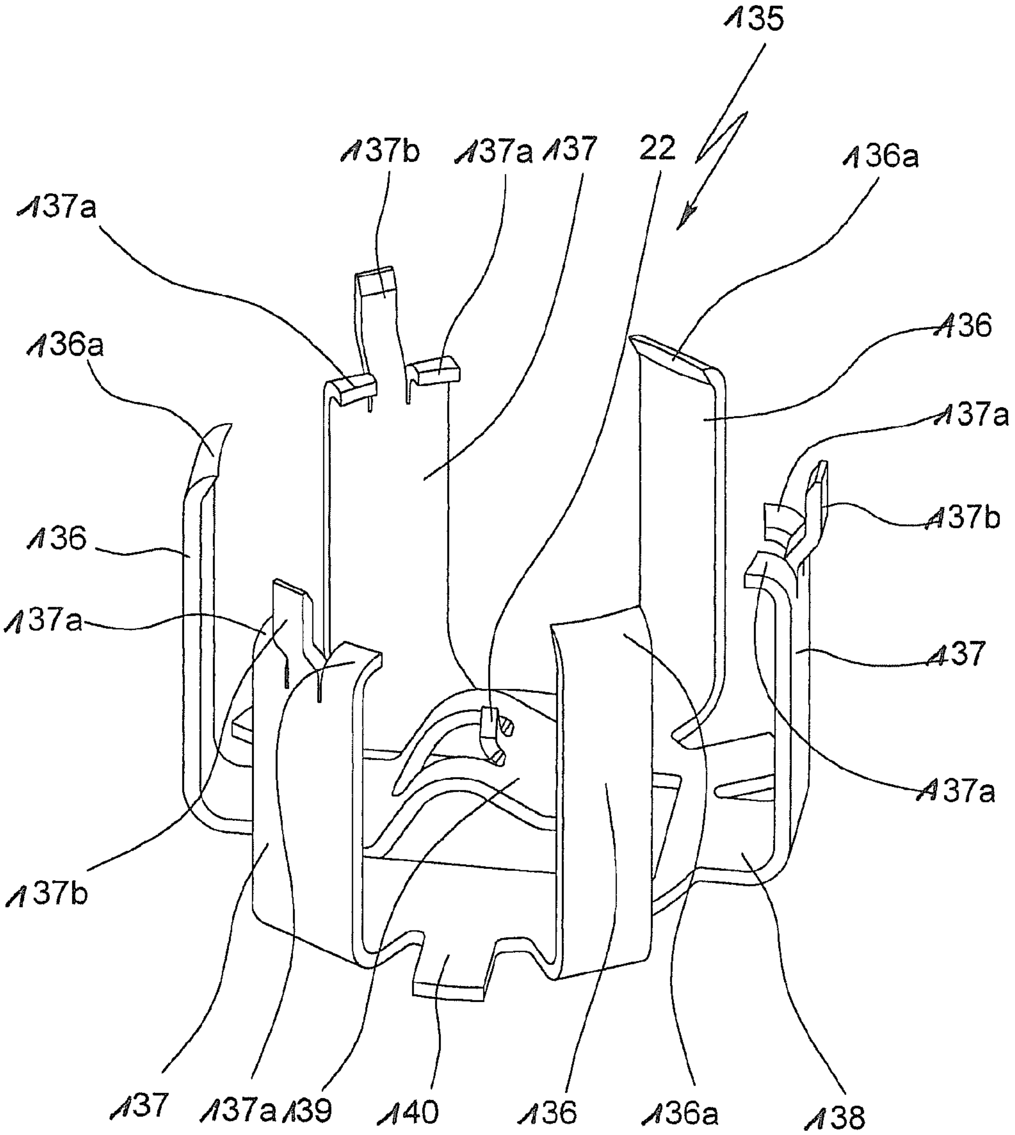
FIG. 30 a perspective view of the securing means.
Figure 31:
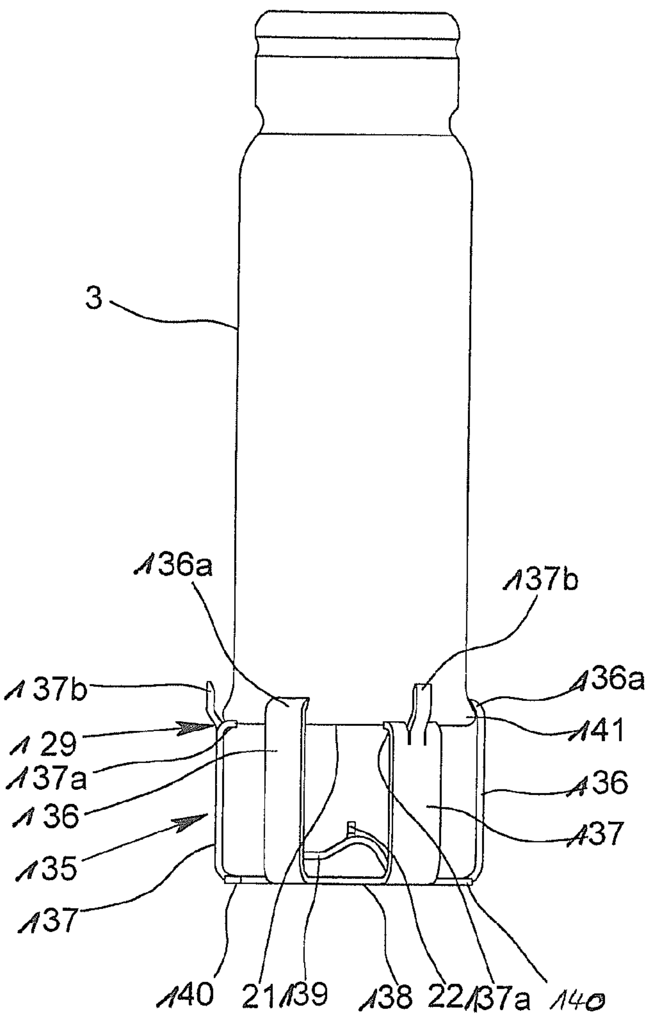
FIG. 31 a side view of the securing means holding the associated container unmoveably.

FIG. 30 shows in a perspective view a preferred embodiment of the securing means 135. FIG. 31 shows the securing means 135 connected with the container 3.

Preferably, the securing means 135 comprises or consists of a metal and/or stamping part and/or consists of a single, unitary part as shown in FIG. 30.

Preferably, the securing means 135 is made of steel, in particular spring steel.

Preferably, the securing means 135 is produced from sheet material by cutting, stamping or the like and/or by bending.

Preferably, the securing means 135 or the part forms a cage, in particular, encompasses the container 3 or an end portion thereof.

Preferably, the securing means 135 comprises holding elements 136 and/or locking elements 137. The elements 136 and 137 are preferably designed like arms, fingers leaves or the like. In particular, the elements 136, 137 are alternately distributed over a circumference of the container 3 and/or extend at least essentially axially or in the direction of the back and forth movement of the container 3.

Preferably, the elements 136 and 137 are held by or connected with a base 138 of the securing means 135.

Preferably, the securing means 135 or base 138 comprises or holds the piercing element 22 for piercing the container 3, i.e. opening the container base 21 or its venting hole 134 in the activated and tensioned state, i.e. when the container 3 reaches its lower end position. In the shown embodiment, the piercing element 22 is formed by a respective bending of a spring portion 139 of the securing means 135 or its base 138. The spring portion 139 can support or facilitate the (complete or final) connection of the container 3 to holder 6.

The securing means 135 or base 138 comprises preferably at least one or multiple fixing portions 140 for fixing the securing means 135 at or in the nebulizer 1 or housing or housing part 18. In particular, the fixing portions 140 may fix the securing means 135 when the securing means 135 is pressed into the housing part 18 by cooperating with the side wall of the housing part 18. However, it is also possible to overmold the securing means 135, its base 138, the fixing portions 140 or the like. Moreover, the securing means 135 could be connected with the housing part 18 or the like in any other suitable manner.

Preferably, the securing means 135 does not only prevent the separation of the container 3 from the nebulizer 1, its housing or housing part 18, but also forms the transportation lock 129 for holding the container 3 unmovable in the housing in the delivery state of the nebulizer 1. FIGS. 29 and 31 shows this state or situation when the container 3 is held (axially) unmovable by the securing means 135, i.e. when the transportation lock 129 is closed. In this situation, the container 3 or its preferably radially protruding end or edge 141 of the container 3 is held between the holding element 136 and locking element 137, in particular between respectively formed or bent ends of the elements 136 and 137.

In the shown embodiment, the container end or edge 141 is caught between end portions 136*a* and 137*a* of the elements 136 and 137. The holding elements 136 grip or extend over the edge 141 and the locking elements 137 or its end portions 137*a* grip or extend under the edge 141 or container base 21 so that the edge 141 and container 3 are securely held preventing any axial movement of the container 3 relative to the securing means 135 and relative to the associated housing part 18 in this state, i.e. with locked securing means 135/transportation lock 129.

The holding element 136 and the locking elements 137 are distributed alterna-tingly around the container 3 or edge 141.

Preferably, the end portions 136*a* of the holding elements 136 end in a first radial plane and the end portions 137*a* of the locking elements 137 end in another, second radial plane, wherein the two planes are axially offset to hold the edge 141 in between and/or wherein the second plane is located axially between the first plane and the lower end position of the container 3 or the lower end of the housing part 18 or the piercing element 22. Additionally or alternatively, the end portions 136*a* end on another radius (outer radius) than the end portions 137*a* and/or are axially spaced therefrom.

The end portions 136*a* and/or 137*a* are preferably form like claws or the like and/or extend preferably radially inwardly.

Preferably, the elements 136 and/or 137 can flex with its free ends radially outwardly.

For example, the ends of the end portions 136*a* may be inclined such that the container 3 may be inserted into or connected with the securing means 135 by a respective axial force so that the holding elements 136 flex outwardly to allow passing of edge 141. However, the holding elements 136 can be flexed outwardly also by a suitable tool (not shown) or the like when the container 3 is inserted, in particular with its edge 141, into the securing means 135.

Preferably, the holding elements 136 prevent separation of the container 3 from the securing means 135 and, thus, from the associated housing part 18 or the like.

The locking elements 137 or its end portions 137*a* can be flexed radially outwardly in order to open the axial holding or transportation lock 129 (this will be explained in detail with reference to FIG. 32 in the following). Then, the container 3 can axially move, in particular back and forth and/or with its edge 141 between the first plane and the piercing element 22 in the present embodiment.

In the present embodiment, the locking elements 137 comprise actuation portions 137*b* (preferably formed at the free ends and/or between adjacent end portions 137*a*). Preferably, the actuation portions 137*b* form axial extensions which may be radially offset. The actuation portion 137*b* cooperate with an associated control member 142 or multiple control members 142 of the nebulizer 1 such that the locking elements 137 are flexed radially outwardly when (completely) closing the housing to open the transportation lock 129 (here primarily formed by the locking elements 137 or its end portions 137*a*).

FIG. 29 shows schematically the control member 142 axially spaced from the associated actuation portion 137*b* as the housing has not yet been closed (completely).

Figure 32:
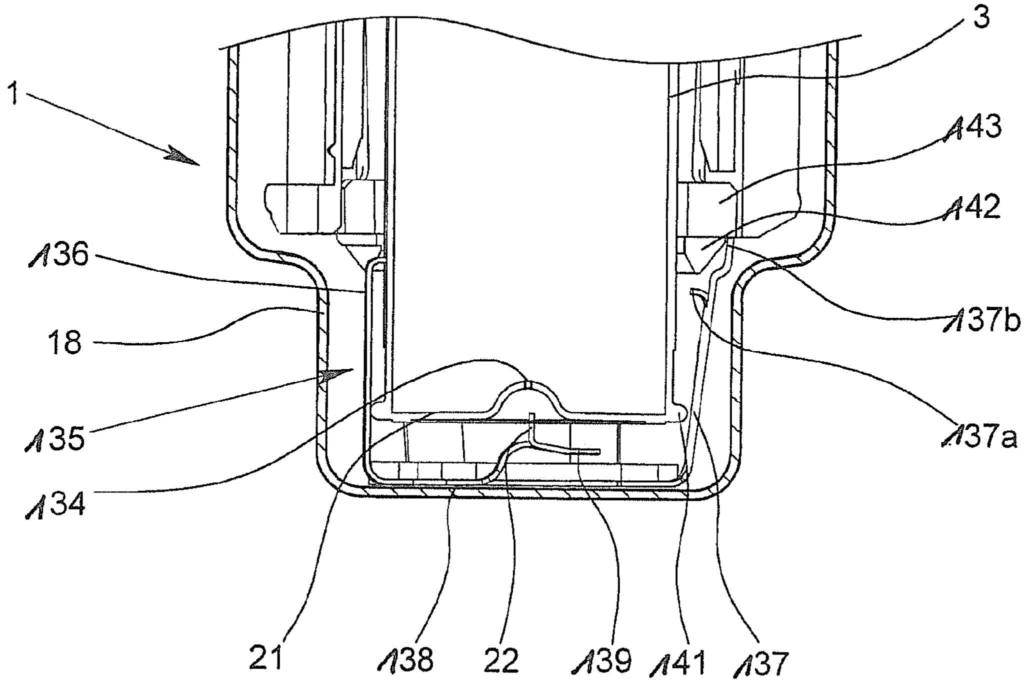
FIG. 32 a schematic partial view of a part of the nebulizer with opened securing means so that the container can move.

FIG. 32 shows a lower part of the completely closed nebulizer 1 with opened transportation lock 129, i.e. with radially outwardly flexed locking elements 137. FIG. 32 shows that the control member 142 has an inclined guiding surface or the like to convert the axial closing movement into the radial opening movement of the actuation portion 137*b* and, thus, of the associated locking element 137 to open the transportation lock 129, in particular when the housing has been completely closed or when the housing part 18 has been pushed completely on the nebulizer 1.

The control member 142 is preferably formed as an axial protrusion. It can be formed by or at a ring 143 or any other bearing means of the nebulizer 1 for counter-bearing the drive spring 7 in the inner part 17 or by or at any other suitable component if the nebulizer such as the inner part 17.

The control member 142 may be formed like an axial protruding ring or shoulder or ridge which extends along the ring 143.

The control member 142 may additionally secure the holding elements 136 against axial opening when the housing is completely closed as schematically shown in FIG. 32. In this case, the control member 142 contacts the holding element(s) 136 or its end portions 136*a* peripherally on the outer side to prevent any outward flexing. Then, the securing means 135 or its holding elements 136 are secured against opening so that the container 3 is securely held within the securing means 135 or the cage formed by the securing means 135 or holding elements 136.

FIG. 32 shows the container 3 in its lower position when the piercing element 22 can pierce the venting hole 134 or an associated seal attached to the container base 21.

In the present embodiment, the securing means 135 has multiple functions. It holds the container 3 (in the activated state/with completely closed housing) such that it can move back and forth, in particular during conveying of the fluid 2, during pressure generation and/or during nebulization, wherein the container 3 is inseparable from the housing or the housing part 18. Further, the securing means 135 forms the transportation lock 129 and/or holds the container 3 unmovable in the delivery state of the nebulizer 1. Additionally or al-ternatively, the securing means 135 comprises an opening means, here the piercing element 22, for opening the venting hole 134 of the container 3.

Preferably, the securing means 135 forms a cage which cannot be separated from the container 3 after connecting it with the container 3.

The transportation lock 129 and the locking elements 137 are kept opened during the normal use of the nebulizer 1, in particular as long as the housing is (completely) closed. When the housing is opened, i.e. the housing part 18 is detached, the control member 142 may disengage from the actuation portions 137*b* so that the locking element 137 can close or flex inwardly again. Then, the locking elements 137 may grip with its end portions 137*a* over the edge 141 of the container 3 such that an additional lock is formed which prevents that the container 3 can be separated from the securing means 135/housing part 18.

The securing means 135 prevents separation of the container 3 from the housing part 18. Therefore, the container 3 can be replaced or exchanged only together with the housing part 18 if the housing part 18 can be detached from the nebulizer 1 or inner part 17 at all. However, it is also possible that the nebulizer 1 can not be opened. Then, the container 3 can not be replaced.

| List of reference numerals | |
|---|---|
| 1 | nebulizer |
| 2 | fluid |
| 3 | container |
| 4 | bag |
| 5 | pressure generator |
| 6 | holder |
| 7 | drive spring |
| 8 | releasing element |
| 9 | conveying tube |
| 10 | non-return valve |
| 11 | pressure chamber |
| 12 | nozzle |
| 13 | mouthpiece |
| 14 | aerosol |
| 15 | air supply opening |
| 16 | upper housing part |
| 17 | inner part |
| 17a | upper part of the inner part |
| 17b | lower part of the inner part |
| 18 | housing part (lower part) |
| 19 | retaining element |
| 20 | spring |
| 21 | container base |
| 22 | piercing element |
| 23 | monitoring device |
| 24 | fluid outlet |
| 25 | first closure |
| 26 | second closure |
| 27 | closure part |
| 28 | flange |
| 29 | transportation lock |
| 31 | latching lug |
| 32 | latching recess |
| 33 | latching arm |
| 34 | vent opening |
| 35 | gripping arm |
| 36 | edge |
| 37 | member |
| 38 | ring |
| 39 | control member |
| 40 | ring portion |

-continued

| List of reference numerals | |
|---|---|
| 41 | actuating portion |
| 42 | mouthpiece cover |
| 43 | latching means |
| 44 | first shoulder |
| 45 | further latching recess |
| 46 | second shoulder |
| 47 | grooves |
| 48 | through hole |
| 49 | indention |
| 50 | actuator |
| 51 | body |
| 51a | half of body |
| 51b | half of body |
| 51c | hinge |
| 52 | stop |
| 53 | handhold |
| 54 | breaking line |
| 54 | start portion |
| 55 | actuator portion |
| 56 | living hinge |
| 57 | cutting edge |
| 58 | bearing |
| 59 | bearing |
| 60 | connecting element |
| 61 | protrusion |
| 62 | glue point |
| 63 | tag |
| 64 | recess |
| 65 | slit |
| 66 | tap |
| 67 | symbol |
| 124 | fluid outlet |
| 125 | first closure |
| 126 | second closure |
| 127 | closure part |
| 128 | flange |
| 129 | transportation lock |
| 131 | latching lug |
| 132 | latching recess |
| 133 | latching arm |
| 134 | venting hole |
| 135 | securing means |
| 136 | holding element |
| 136a | end portion |
| 137 | locking element |
| 137a | end portion |
| 137b | actuation portion |
| 138 | base |
| 139 | spring portion |
| 140 | fixing portion |
| 141 | edge |
| 142 | control member |
| 143 | ring |
| 144 | ring portion |
| 145 | corrugation |

The invention claimed is:

1. A nebulizer forming an inhaler, comprising:

a first housing part and a second housing part forming a housing, where the first and second housing parts are axially slidable in a longitudinal direction relative to one another between a delivery state and an activated state;

a container, containing a fluid, disposed within the housing such that: (i) in the delivery state the first and second housing parts are sufficiently axially separated such that the fluid within the container is not accessed, and (ii) in the activated state the first and second housing parts are sufficiently axially proximate such that the fluid within the container is accessed;

a securing member operating to prevent the first housing part and second housing part to move axially from the delivery state to the activated state, the securing member including an actuator for grasping by a user to open, remove, release or destroy the securing member, and the securing member including a body having a predetermined, weakened breaking line extending in a continuously curved fashion and including at least one of: (i) a reduction in a thickness of the material of the body, and (ii) a perforation in the material of the body, wherein the securing member must be manually opened, removed, released or destroyed by tearing the body of the securing member along the breaking line, and thereby permit the first housing part and second housing part to move axially from the delivery state to the activated state, and wherein the weakened breaking line includes a substantially axially extending section in the longitudinal direction, which transitions to a substantially circumferentially extending section as the weakened breaking line extends in the continuously curved fashion.

2. The nebulizer according to claim 1, wherein the securing member is molded as one integral piece with the actuator.

3. The nebulizer according to claim 1, wherein the actuator is non-detachable from the securing member.

4. The nebulizer according to claim 1, wherein the actuator includes a grasping element, including at least one of a handhold, a grip, a lever, a tag, a flap, a ring, and a clip to facilitate grasping by the user.

5. The nebulizer according to claim 1, wherein the nebulizer comprises an outlet end or mouthpiece, and the actuator is located adjacent to the outlet end or mouthpiece in the delivery state.

6. The nebulizer according to claim 1, wherein the nebulizer comprises a mouthpiece cover, and the actuator is located at least one of: adjacent to, at least partially below, and at least partially above the mouthpiece cover in the delivery state.

7. The nebulizer according to claim 1, wherein the nebulizer comprises a releasing element operating to permit a dose of the fluid to be nebulized, and the actuator is located at least one of: adjacent to, above, and around the releasing element in the delivery state.

8. The nebulizer according to claim 4, wherein the nebulizer comprises a releasing element operating to permit a dose of the fluid to be nebulized, and the actuator or the grasping element thereof is located at least one of partially above, and on, the releasing element so that the user tends to actuate the actuator before pressing the releasing element.

9. The nebulizer according to claim 1, further comprising a conveying tube, operating to access the fluid within the container, before or during first use of the nebulizer, when the first and second housing parts are axially located in the activated state by insertion of the conveying element into the container, wherein the conveying tube operates to convey the fluid from the container.

10. The nebulizer according to claim 1, further comprising a latching means having at least one latching lug for securing the first and second housing parts against detachment when in the delivery state and in the activated state, wherein the first and second housing parts may attain a loading rotational position, differing from a rotational position of the delivery state, whereby the first and second housing parts may be detached for inserting the container.

11. The nebulizer according to claim 1, wherein the securing member comprises inner radial protrusions or ribs forming axial stops for preventing the first and second housing parts from moving axially towards one another while in the delivery state.

12. The nebulizer according to claim 1, wherein the securing member forms at least one of a loop, ring, sleeve and banderole.

13. The nebulizer according to claim 1, wherein the securing member comprises a hinge for opening the securing member.

14. The nebulizer according to claim 1, wherein the actuator is formed by at least one of: a self-adhesive tap, a self-adhesive tag, a self-adhesive label, a self-adhesive tape, a flexible material, and a foil-like material.

15. The nebulizer according to claim 1, wherein the actuator includes a ring-shaped hold for grasping by the user to facilitate the opening, removing, releasing or destroying of the securing member along the weakened breaking line.

16. The nebulizer according to claim 1, wherein the substantially axially extending section and the substantially circumferentially extending section define a helical path as the weakened breaking line extends in the continuously curved fashion.

17. The nebulizer according to claim 1, wherein the actuator is also continuously curved and complements the continuous curvature of the weakened breaking line.

18. A nebulizer forming an inhaler, comprising:

a first housing part and a second housing part forming a housing, where the first and second housing parts are axially slidable in a longitudinal direction relative to one another between a delivery state and an activated state;

a container, containing a fluid, disposed within the housing such that: (i) in the delivery state the first and second housing parts are sufficiently axially separated such that the fluid within the container is not accessed, and (ii) in the activated state the first and second housing parts are sufficiently axially proximate such that the fluid within the container is accessed;

a securing member operating to prevent the first housing part and second housing part to move axially from the delivery state to the activated state, the securing member including a body having a pre-determined, weakened breaking line extending in a continuously curved fashion and including at least one of: (i) a reduction in a thickness of the material of the body, and (ii) a perforation in the material of the body, wherein the securing member must be manually opened, removed, released or destroyed by tearing the body of the securing member along the breaking line, and thereby permit the first housing part and second housing part to move axially from the delivery state to the activated state, and wherein the weakened breaking line includes a substantially axially extending section in the longitudinal direction, which transitions to a substantially circumferentially extending section as the weakened breaking line extends in the continuously curved fashion.

19. The nebulizer according to claim 18, wherein the securing member is molded as one integral piece with an actuator.

20. The nebulizer according to claim 18, wherein an actuator is non-detachable from the securing member.

21. The nebulizer according to claim 18, wherein the securing member includes a grasping element, including at least one of a handhold, a grip, a lever, a tag, a flap, a ring, and a clip to facilitate grasping by the user.

22. The nebulizer according to claim 18, wherein the securing member includes an actuator for grasping by the user to open, remove, release or destroy the securing member.

23. The nebulizer according to claim 22, wherein at least one of:

the nebulizer comprises an outlet end or mouthpiece, and the actuator is located adjacent to the outlet end or mouthpiece in the delivery state; and the nebulizer comprises a mouthpiece cover, and the actuator is located at least one of: adjacent to, at least partially below, and at least partially above the mouthpiece cover in the delivery state.

24. The nebulizer according to claim 22, wherein the nebulizer comprises a releasing element operating to permit a dose of the fluid to be nebulized, and the actuator is located at least one of: adjacent to, above, and around the releasing element in the delivery state.

25. The nebulizer according to claim 22, wherein the nebulizer comprises a releasing element operating to permit a dose of the fluid to be nebulized, and the actuator or the grasping element thereof is located at least one of partially above, and on, the releasing element so that the user tend to actuate the actuator before pressing the releasing element.

26. The nebulizer according to claim 18, further comprising a conveying tube, operating to access the fluid within the container, before or during first use of the nebulizer, when the first and second housing parts are axially located in the activated state by insertion of the conveying element into the container, wherein the conveying tube operates to convey the fluid from the container.

27. The nebulizer according to claim 18, further comprising a latching means having at least one latching lug for securing the first and second housing parts against detachment when in the delivery state and in the activated state, wherein the first and second housing parts may attain a loading rotational position, differing from a rotational position of the delivery state, whereby the first and second housing parts may be detached for inserting the container.

28. The nebulizer according to claim 18, wherein the securing member comprises inner radial protrusions or ribs forming axial stops for preventing the first and second housing parts from moving axially towards one another while in the delivery state.

29. The nebulizer according to claim 18, wherein the securing member forms at least one of a loop, ring, sleeve and banderole.

30. The nebulizer according to claim 18, wherein the securing member comprises a hinge for opening the securing member.

31. The nebulizer according to claim 18, further comprising an actuator which is formed by at least one of: a self-adhesive tap, a self-adhesive tag, a self-adhesive label, a self-adhesive tape, a flexible material, and a foil-like material.

32. The nebulizer according to claim 18, further comprising an actuator which includes a distal portion sized and shaped for the user to grasp and an elongate portion extending from the distal portion, and wherein the elongate portion is at least partially circumscribed by the breaking line.

* * * * *